(12) United States Patent
Drasar et al.

(10) Patent No.: US 9,393,200 B2
(45) Date of Patent: Jul. 19, 2016

(54) LIPOPOLYAMINES OF SPERMINE TYPE FOR CONSTRUCTION OF LIPOSOMAL TRANSFECTION SYSTEMS

(71) Applicants: USTAV ORGANICKE CHEMIE A BIOCHEMIE AV CR, V.V.I., Praha (CZ); VYZKUMNY USTAV VETERINARNIHO LEKARSTVI, V.V.I., Brno (CZ)

(72) Inventors: Lukas Drasar, Praha (CZ); Miroslav Ledvina, Praha (CZ); Zina Korvasova, Brno (CZ); Jaroslav Turanek, Brno (CZ)

(73) Assignees: USTAV ORGANICKE CHEMIE A BIOCHEMIE AV CR, V.V.I., Praha (CZ); VYZKUMNY USTAV VETERINARNIHO LEKARSTVI, V.V.I., Brno (CZ)

( * ) Notice: Subject to any disclaimer, the term of this patent is extended or adjusted under 35 U.S.C. 154(b) by 112 days.

(21) Appl. No.: 14/370,526

(22) PCT Filed: Jan. 14, 2013

(86) PCT No.: PCT/CZ2013/000004
§ 371 (c)(1),
(2) Date: Jul. 3, 2014

(87) PCT Pub. No.: WO2013/104346
PCT Pub. Date: Jul. 18, 2013

(65) Prior Publication Data
US 2015/0018436 A1    Jan. 15, 2015

(30) Foreign Application Priority Data

Jan. 13, 2012 (CZ) ..................... 2012-20

(51) Int. Cl.
| | |
|---|---|
| *A61K 9/127* | (2006.01) |
| *C07C 233/18* | (2006.01) |
| *C07C 233/35* | (2006.01) |
| *C07J 41/00* | (2006.01) |
| *A61K 47/18* | (2006.01) |
| *C12N 15/88* | (2006.01) |
| *C07J 9/00* | (2006.01) |

(52) U.S. Cl.
CPC ............... *A61K 9/1272* (2013.01); *A61K 47/18* (2013.01); *C07C 233/18* (2013.01); *C07C 233/35* (2013.01); *C07J 9/00* (2013.01); *C07J 41/0055* (2013.01); *C12N 15/88* (2013.01)

(58) Field of Classification Search
CPC ....................................................... A71K 9/1272
USPC .................. 514/788; 552/544; 554/36, 51
See application file for complete search history.

(56) References Cited

U.S. PATENT DOCUMENTS

| | | | | |
|---|---|---|---|---|
| 8,653,049 B2* | 2/2014 | Hipler | .................... | A61K 39/39 514/23 |
| 2010/0260830 A1* | 10/2010 | Salvatore | ............. | A61K 9/1272 424/450 |
| 2011/0002983 A1* | 1/2011 | Hipler | .................... | A61K 39/39 424/450 |
| 2015/0018436 A1* | 1/2015 | Drasar | ................. | A61K 9/1272 514/788 |

OTHER PUBLICATIONS

G. Byk. et al., Synthesis, activity and 1,2,4,5, structure-activity relationship studies of 8,9 novel cationic lipids for DNA transfer, Journal of Medicinal Chemistry, vol. 41, No. 2, Jan. 1998, p. 224-235, American Chemical Society, Washington, DC.

M.A. Maslov, et al., Novel cholesterol spermine conjugates provide efficient cellular delivery of plasmid DNA and small interfering RNA, Journal of Controlled Release, vol. 160, No. 2, Nov. 2011, p. 182-193, Elsevier, Amsterdam, NL.

R.G. Cooper, et al.: 11 Polyamine analogues of 3beta-[(N',N'-dimethylaminoethane) carbamoyl] -cholesterol (DC-chol) as agents for gene delivery, Chemistry—A European Journal, vol. 4, No. I, Jan. 1998, p. 137-151, Verlag, Weinheim, DE.

International Search Report and Written Opinion for PCT/CZ2013/000004 filed Jan. 14, 2013.

\* cited by examiner

*Primary Examiner* — Sabiha N Qazi
(74) *Attorney, Agent, or Firm* — Notaro, Michalos & Zaccaria P.C.

(57) ABSTRACT

The invention provides new lipopolyamines of spermine type of the general formula I, wherein X is C—N bond or aminopolyethyleneglycolcarboxamide linker or o-hydroxy-alkylcarboxamide linker or ω-hydroxyalkylcarboxamidopolyethyleneglycol-carboxamide linker, and wherein a hydrophobic domain Y is an acyl symmetrically branched in the position C(2) or cholesteryl. The invention further provides a method of preparation of said lipopolyamines and their use for construction of polycationic liposomal drug carriers.

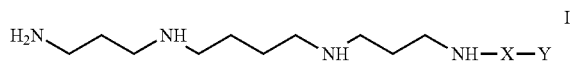

5 Claims, 6 Drawing Sheets

LIPOPOLYAMINES OF SPERMINE TYPE FOR CONSTRUCTION OF LIPOSOMAL TRANSFECTION SYSTEMS

FIELD OF ART

The invention relates to new lipopolyamines, a method of their synthesis and use of these compounds for construction of polycationic self-assembling drug carriers based on negatively charged fragments of nucleic acids.

BACKGROUND ART

One of the main problems, which currently limit the application of gene therapy and genetic vaccines into common clinical practice, is the insufficient transporting efficiency of nucleic acid (NA) fragments through the cell wall and their following internalization into the cell nucleus, the so-called transfection (Miller, A. D. 2004; Zhang, S. B. et al. 2010). In this case, the drug is a fragment of negatively charged nucleic acid, which must be able to penetrate through the cell and nuclear membranes. It is essentially a gene correction by insertion of (a) correcting gene(s) and reduction of activity of unsuitable genes. DNA vaccines represent a specific area of gene therapy, in which the target cells are antigen presenting cells of the immune system (especially dendritic cells and monocytes; Saha, R. et al. 2011).

The penetration of the negatively charged NA fragment through the phospholipid bilayer of the cell wall plays a key role in this process. In the last decade, this fact has initiated a broad and intensive research focused on the development of carriers (vectors) that would be able to effectively transport the NA through the cell membrane. These vectors must also guarantee the protection of the NA from its degradation in vivo (Kirby, A. J. et al. 2003; Miller, A. D. 1998; Zhang, S. B. et al. 2010). The problem of cell membrane transport efficiency occurs also in the case of nucleotide and oligonucleotide antineoplastics and antivirotics (Holý, A. 2003).

The methods for transport of the NA fragment into the target cells use either viral or nonviral vectors. Today, the viral vectors represent the most effective transfection system. Unfortunately, due to possible biological risks (especially unpredictable immune reactions), the introduction of viral vectors into a regular clinical practice is very problematic (Miller, A. D. 1992; Zhang, S. B. et al. 2010). The nonviral vectors can be divided into physical and chemical vectors, according to the method of transporting the NA into the intracellular space. The physical vectors use physical or mechanical disruption of the cell membrane. This enables the insertion of the NA into the intracellular space (Andre, F. M. et al. 2010). The chemical vectors are based on polycationic polymers or on supramolecular self-assembling lipidic systems, which form a complex (polyplex, resp. lipoplex) with the negatively charged NA, wherein the complex can pass through the cell membrane and also protects the NA from the degradation in bloodstream. The most often used cationic polymers are DEAE-dextran (Ohtani, K. et al. 1989), chitosan (Hejazi, R. et al. 2003; Koping-Hoggard, M. et al. 2001), polylysine (Lemaitre, M. et al. 1987), polyethylenimine (Boussif, O. a spol. 1995), and polyamine dendrimers, respectively (Haensler, J. et al. 1993).

At present, polycationic self-assembling lipidic systems (polycationic liposomes) seem to be promising candidates for NA carriers, applicable in human medicine. They are most often formed by synthetic lipopolyamine (so-called cytofectine) and a neutral colipid. Polycationic liposomes, in contrast to viral vectors, are composed from structurally defined molecules and therefore their physical and biological properties can be modulated by structural changes with the aim to increase the transfection ability and to suppress their toxicity. This fact initiated an extensive research in the area of polycationic lipids. Many cationic lipids differing in the character of cationic and hydrophobic domains were prepared (Niculescu-Duvaz, D. et al. 2003; Zhi, D. F. et al. 2010). Many of these cationic lipids are now commercially available as transfection agents and several liposomal formulations were used in clinical tests in gene therapy of cancer and other genetic diseases (Behr, J. P. 1994).

From the structural point of view, the cationic domains represent cationic lipids, the domain of which is composed of polyamines derived from natural spermine or spermidine. They form the most successful class of cationic lipids. Their activity is due to an effective neutralization, precipitation and encapsulation of DNA, and their endosomal and buffering properties (Stewart, L. et al. 2001). Other often occurring cationic domains are, e.g., quaternary ammonium ions, guanidinium motive, nitrogen containing heterocycles, basic amino acids, and short peptides derived therefrom (Niculescu-Duvaz, D. et al. 2003). Hydrophobic domains usually contain one or more aliphatic chains (saturated, unsaturated or fluorinated), or a steroid residue.

The overall geometry of the cationic lipid, i.e. the ratio of the polar and the nonpolar part of the molecule, has a fundamental influence on the formation of structural phases in solution and on the transfection activity. Two-chain lipids, in comparison with the single-chain or three- or multiple-chain lipids, more easily form lipidic bilayers, which close itself into spherical liposomes in water solution. On the other hand, cationic lipids containing one or three aliphatic chains have an increased tendency to form micelles or reverse micells and therefore they show a lower transfection activity and often an increased toxicity (Niculescu-Duvaz, D. et al. 2003; Tsukamoto, M. et al. 1995). Therefore, an overwhelming majority of commonly used cationic lipids contains two aliphatic chains. The most commonly used branching domain is glycerol, which, like in natural amphiphiles, serves for the presentation of two hydrophobic chains (Zuhorn, I. S. et al. 2002). Cationic lipids having this structure can be symmetrical or asymmetrical, depending on the place where the hydrophobic domain is bound. Synthetically easily obtainable secondary amides of amino acids represent an interesting branching principle enabling presentation of two hydrophobic chains (Behr, J. P. et al. 1989). Other structural motives, suitable for multiple presentation of hydrophobic domains, are, e.g., substituted aromatic rings and short peptides (for review see ref. Niculescu-Duvaz, D. et al. 2003). A specific group of hydrophobic domains are sterols with planar structure. Lipids containing a steroidal unit have the tendency to strengthen the lipidic bilayer (Regelin, A. E. et al. 2000). They are mostly derivatives of cholesterol with polycationic domain of polyamine type which are bound in position C(3) via urethane group. Into this category belongs also the commercially available C-DAN (Gao, X. et al. 1991; Keller, M. et al. 2003; Petukhov, I. A. et al. 2010). A broader application of these cationic lipids is limited by the restrained stability of their urethane connecting group. Transfection systems can be based also on amides of cholic acids (Fujiwara, T. et al. 2000).

DISCLOSURE OF THE INVENTION

This invention solves the problems of: (a) difficulties in the synthesis of lipopolyamines containing two symmetrical aliphatic hydrophobic domains, based on symmetrical lipophilic diacylderivatives of glycerol and on symmetrical secondary amino acid amides, respectively, by the use of amides of synthetically easily available fatty acids symmetrically branched in position C(2), as well as the insertion of polyethylene glycol linker between hydrophobic and polycationic domain; (b) the limited stability of urethane linker in lipopolyamines derived from cholesterol by its replacement by a linker composed of amides of ω-hydroxycarboxyl acids or aminopolyethyleneglycolcarboxylic acids.

The subject-matter of the invention are lipopolyamines of spermine type of the general formula I,

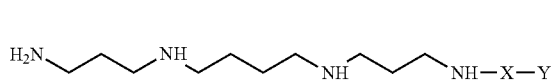

I wherein X is a C—N bond or aminopolyethyleneglycolcarboxamide linker of the general formula II,

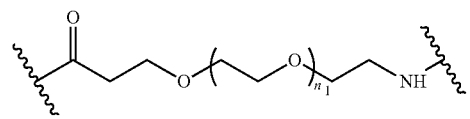

II wherein $n_1$=1-13,
or ω-hydroxyalkylcarboxamide linker of the general formula III

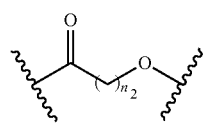

III wherein $n_2$=1-9,
or ω-hydroxyalkylcarboxamidopolyethyleneglycolcarboxamide linker of the general formula IV

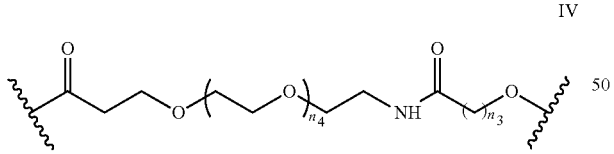

IV wherein $n_3$=1-9 and $n_4$=1-13,
and the hydrophobic domain Y is an acyl of the general formula V symmetrically branched in the position C(2)

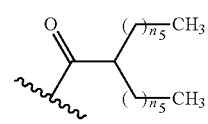

V wherein $n_5$=5-30, or cholesteryl ((3β)-cholest-5-en-3-yl) of the formula VI

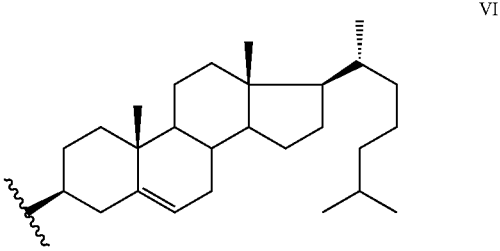 [SMILES: *[C@H]1CC[C@@]2(C)C(=CCC3C2CC[C@@]2(C)C3CC[C@@H]2[C@H](C)CCCC(C)C)C1]

VI provided that:
when X is C—N or aminopolyethyleneglycolcarboxamide linker of the general formula II, then Y is the acyl of the general formula V symmetrically branched in the position C(2), and when X is ω-hydroxyalkylcarboxamide linker of the general formula III or ω-hydroxyalkylcarboxamidopolyethyleneglycolcarboxamide linker of the general formula IV, then Y is cholesteryl ((3β)-cholest-5-en-3-yl) of the general formula VI.

In a preferred embodiment of the invention, in the lipopolyamines of spermine type of the general formula I X=C—N bond or a linker of the general formula II, wherein $n_1$=3, and Y=acyl of the general formula V, wherein $n_5$=13.

Preferably, the compounds of the general formula I have X=linker of the general formula III, wherein $n_2$=1 or 3, or X=linker of the general formula IV, wherein $n_3$=1 or 3, $n_4$=3, and Y is cholesteryl of the formula VI.

Another object of the invention is a method of preparation of lipopolyamines of spermine type of the general formula I. The synthesis is based on condensation of commercially available $N^2N^3N^4$-tri-(tert-butoxycarbonyl)spermine with pentafluorophenylesters of fatty acids symmetrically branched in position C(2) of the general formula VII

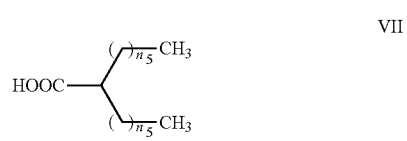

VII wherein $n_1$=5-30 (obtainable in accordance with lit., Kusumoto, S. et al., 78), or of acids of the general formula VIII,

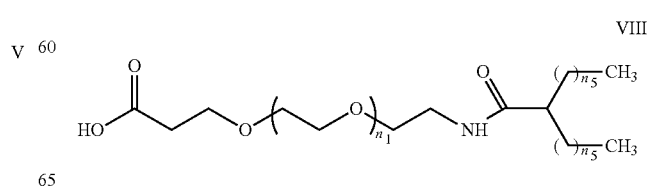

VIII wherein $n_1$=1-13 and $n_5$=5-30, or of acids of the general formula IX

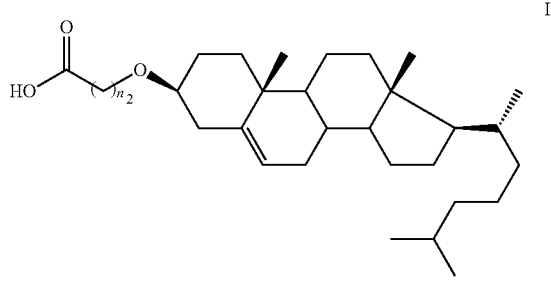

wherein $n_2=1-9$, or
of acids of the general formula X

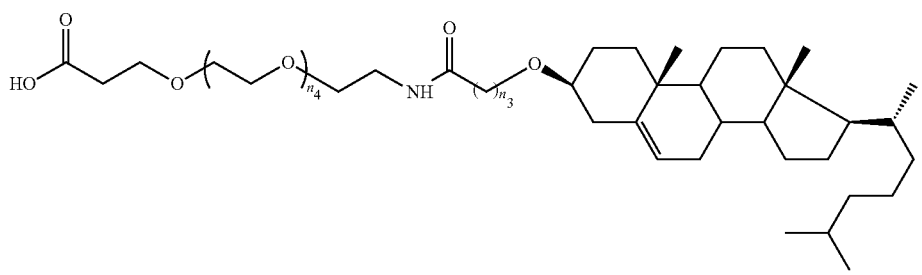

wherein $n_3=1-9$ and $n_4=1-13$;
where
the acid of the general formula VII, VIII, IX or X is reacted with bis(pentafluorophenyl)carbonate in the presence of an organic base in a polar aprotic solvent (preferably in the presence of 4-methylmorpholine in N,N-dimethylformamide) to form the corresponding pentafluorophenylesters. The reaction of the obtained acid pentafluorophenylesters with $N^2N^3N^4$-tri-(tert-butoxycarbonyl)spermine in the presence of an organic base in a polar aprotic solvent (preferably in the presence of ethyldiisopropylamine in N,N-dimethylformamide) affords protected polycationic lipids of the general formula XI,

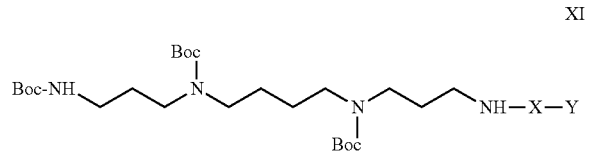

wherein X is C—N or aminopolyethyleneglycolcarboxamide linker of the general formula II, or ω-hydroxyalkylcarboxamide linker of the general formula III, or ω-hydroxyalkylcarboxamidopolyethyleneglycolcarboxamide linker of the general formula IV and Y is acyl of the general formula V, or cholesteryl ((3β)-cholest-5-en-3-yl) of the formula VI, provided that:
  when X is C—N or aminopolyethyleneglycolcarboxamide linker of the general formula II, then Y is the acyl of the general formula V symmetrically branched in the position C(2), and
  when X is ω-hydroxyalkylcarboxamide linker of the general formula III or ω-hydroxyalkylcarboxamidopolyethyleneglycolcarboxamide linker of the general formula IV, then Y is cholesteryl ((3β)-cholest-5-en-3-yl) of the general formula VI.

Hydrolytic cleavage of tert-butoxycarbonyl protecting groups (so called debocylation) from the compounds of the general formula XI (preferably using trifluoroacetic acid in dichloromethane) affords lipopolyamines of the general formula I.

Acids of the general formula VIII are prepared by reaction of pentafluorophenylesters of acids of the general formula VII with aminopolyethyleneglycolcarboxylic acids {$H_2N$—$(CH_2)_2$—[O—$(CH_2)_2$]$_n$—O—$(CH_2)_2$—COOH, n=1-13} in the presence of an organic base in a polar aprotic solvent (preferably in the presence of ethyldiisopropylamine in N,N-dimethylformamide).

Acids of the general formula IX are prepared by: (a) base catalyzed alkylation of commercially available cholesterol by tert-butylester of ω-bromoalkane acids having $C_2$-$C_{10}$ carbon atoms in an aprotic solvent followed by acidic cleavage (preferably using formic acid in diethylether) of the obtained tert-butylesters of the general formula XII

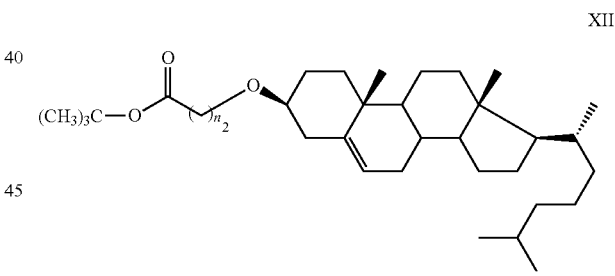

wherein $n_2=1-9$;
(b) reaction of commercially available O-tosyl derivative of cholesterol [(3β-cholest-5-en-3-yloxy-4-methylbenzenesulfonate] with ω-hydroxyalkanenitriles having $C_2$-$C_{10}$ carbon atoms in a nonpolar aprotic solvent at increased temperature (preferably in boiling toluene) followed by basic hydrolysis (preferably in a mixture of toluene and aqueous solution of NaOH at elevated temperature) of the intermediary O-[(3β)-cholest-5-en-3-yl]-ω-hydroxyalkanenitrile.

Acids of the general formula X are prepared by the reaction of pentafluorophenylesters of acids of the general formula IX with aminopolyethyleneglycolcarboxylic acids {$H_2N$—$(CH_2)_2$—O—[$(CH_2)_2$—O]n-$(CH_2)$—COOH, n=1-13} in the presence of an organic base in an organic aprotic solvent (preferably in the presence of ethyldiisopropylamine in N,N-dimethylformamide).

The subject-matter of the invention is also the use of lipopolyamines of spermine type of the general formula I for construction of polycationic self-assembling systems, i.e., polycationic liposomal drug carriers, wherein the drugs are based on negatively charged nucleic acid fragments. The drugs may include nucleotide and oligonucleotide therapeutics and therapeutic gene constructs.

The ability of polycationic liposomes constructed on the basis of polycationic lipids of the general formula I to effectively transport nucleotide and oligonucleotide therapeutics and therapeutic gene constructs across the cell membrane was verified in the following in vitro tests.
(a) By increasing the antiviral activity of the nucleotide antivirotic Cidofovir towards the infection of MDBK cells by bovine herpesvirus BHV-1.
(b) By transport of fluorescently labelled model oligonucleotides into MCF-7 cells.
(c) By efficiency of the transfection of MCF-7 cells by a plasmide encoding the enzyme luciferase.

EXAMPLES OF CARRYING-OUT THE INVENTION

List of Abbreviations

Figure 1:
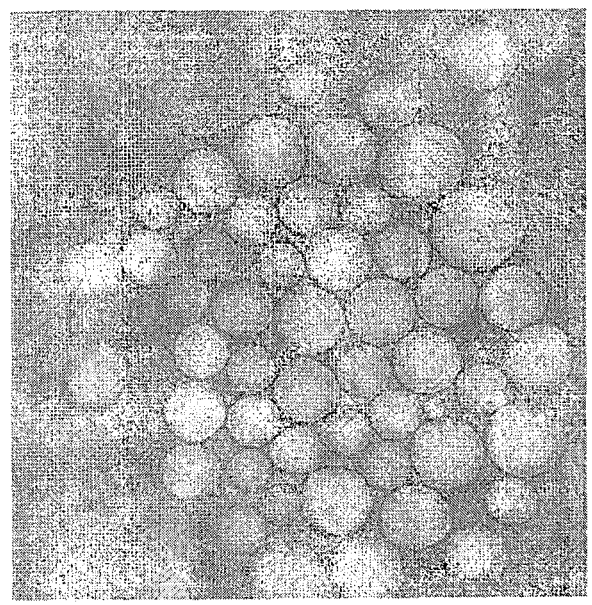
FIG. 1: Photograph of liposomes with 20% content of cationic lipid 1 from transmission electron microscope.

TLC Thin layer chromatography
HR-MS High-resolution mass spectrometry
NMR Nuclear magnetic resonance
PBS Phosphate buffered saline
MEM Minimal essential medium
Cells MDBK Madin-Darby Bovine Kidney Cells
MTT test Test cell viability based on reduction of MTT to formazan
QRT-PCR Quantitative Real-Time Polymerase Chain Reaction
Buňky MCF7 Estrogen responsive human breast adenocarcinoma cell line Example 1

To a stirred solution of 2-tetradecylhexadecanoic acid (formula VII where $n_5$=13; 51.5 mg, 0.11 mmol) in dry N,N-dimethylformamide (4 mL), bis(pentafluorophenyl) carbonate (49 mg, 0.12 mmol) and 4-methylmorpholine (0.1 mL, 1 mmol) were added and the stirring was continued at room temperature for 1 h. The mixture was lyophilized from dioxane (2×20 mL), to give pentafluorophenyl ester of 2-tetradecylhexadecanoic acid (67 mg), which was immediately used at next condensation step.

A mixture of pentafluorophenyl ester of 2-tetradecylhexadecanoic acid and $N^2N^3N^4$-tri-(tert-butoxycarbonyl)spermine (49 mg; 0.079 mmol) was dried in an apparatus equipped with septum for 4 h at room temperature and 0.1 Pa and then the apparatus was flushed with argon (2×). Dry N,N-dimethylformamide (4 ml) and N-ethyldiisopropylamine (0.5 ml) were added through the septum and the mixture was stirred at room temperature for 12 h. Flash chromatography of the crude reaction mixture on the silica gel column (100 ml) in toluene-ethyl acetate (gradient: 0-40% ethyl acetate, 10 ml/min, 160 min) gave (75 mg; 82%) $N^1$-(2-Tetradecylhexadecanoyl)-$N^4$,$N^9$,$N^{12}$-tri-tert-butoxycarbonyl-1,12-diamino-4,9-diazadodecane (formula XI; X═C—N bond; Y=hydrophobic domain of the general formula V, where $n_5$=13). $^1$H NMR (400 MHz, CDCl$_3$) δ (ppm): 3.00-3.37 m, 12H (CH$_2$N—) 1.90-2.11 m, 1H (CHCOO); 1.56-1.73 m, 8H (CH$_2$CH$_2$N—); 1.36-1.55 m, 27H (tert-butyl); 1.17-1.34 m, 52H 0.80-0.94 m, 6H (2-Tetradecylhexadecanoyl); $^{13}$C NMR (101 MHz, CDCl$_3$) δ (ppm): 176.01 (C-1') 129.01, 128.19, 125.27 (NCOO) 83.60 (s, 1C) 79.68 3C (CCH$_3$) 48.16 (C-2') 46.64 4C (C-4, C-6, C-9, C-11) 33.09 2C (C-2, C-13, C-3', C-1") 31.95, 31.93, 31.91, 31.89 4C (C-5', C-14', C-3", C-12") 29.1-29, 3 m 16C (C6'-13', C4"-11") 28.37-28.50 m, 9C (CCH$_3$) 28.45 br. s 4C(C-3, C-7, C-8, C-12) 22.66 s 2C (C-15', C-13") 14.08 s 2C (C-16', C-14"); for $C_{55}H_{108}N_4O_7$ monoisotopic mass: calculated: 936.8. found: MS ESI m/z: 959.7 [M+Na]+. for $C_{55}H_{108}N_4O_7$ calculated: 70.47% C; 11.61% H; 5.98% N. found: 70.12% C; 11.47% H; 5.70% N. for $C_{55}H_{108}N_4O_7$—Na+ HR-MS calculated: 937.8291. found: 937.8297; IR (CHCl$_3$): 1392, 1368, 1248, 1165, 863 (tert-butyl); 3452, 3357, 1704, 1608.

Example 2

To a solution of $N^1$-(2-Tetradecylhexadecanoyl)-$N^4$,$N^9$,$N^{12}$-tri-tert-butoxycarbonyl-1,12-diamino-4,9-diazadodecane (formula XI; X═C—N bond; Y=hydrophobic domain of the general formula V, where $n_5$=13; 253 mg, 0.26 mmol) in dichloromethane (5 ml), trifluoroacetic acid (2 ml, 26 mmol) was added and the mixture was stirred at room temperature for 4 h. The mixture was evaporated in vacuo and the residue was lyophilized from dioxane (20 ml) to afford 171 mg of compound $N^1$-(2-tetradecylhexadecanoyl)-1,12-diamino-4,9-diazadodecane (formula I; X═C—N bond; Y=hydrophobic domain of the general formula V, where $n_5$=13). $^1$H NMR (400 MHz, Acetone-d6) δ (ppm): 3.98 t, J=6.25 Hz, 2H (CH$_2$-2); 3.36 t, J=6.13 Hz, 2H (CH$_2$-6); 3.27-3.32 m, 2H (CH$_2$-9); 3.13-3.21 m, 6H (CH$_2$-11, CH$_2$-4); 3.10 t, J=6.63 Hz, 2H (CH$_2$-13); 2.31-2.38 m, 1H (CH-2'); 1.93-2.03 m, 6H (CH$_2$-3, CH$_2$-7, CH$_2$-8); 1.53-1.62 m, 2H (CH$_2$-12); 1.35-1.43 m, 4H (CH$_2$-3', CH$_2$-1"); 1.28 s, 36H (CH24'-16', CH21-13"); 0.88 t, J=7.00 Hz, 6H (CH2-17', CH2-14"); $^{13}$C NMR (101 MHz, Acetone-d6) δ (ppm): 178.36 (C-1'); 47.70 (C-2') 47.51 (C-11); 45.80 (C-4); 45.63 (C-6); 44.45 (C-9); 39.24 (C-13); 36.07 (C-2); 33.80 (C-12); 32.73 2C(CH2-3', CH2-1") 30.55; 30.47; 30.46; 30.36; 30.17; 29.97; 28.43 2C(CH$_2$-4', CH$_2$-2") 27.28 (C-3); 24.43 (C-7); 23.62 (C-8); 23.41 2C (CH$_2$-16', CH$_2$-13") 14.43 2C (2×CH$_3$); for $C_{40}H_{84}N_{40}$ monoisotopic mass: calculated: 636.6. found: MS ESI m/z: 637, 6 [M+H]+; for $C_{40}H_{84}N_4O$—H$^+$ HR-MS, calculated: 637.67179. found: 637.67117; IR (CHCl3): 3263, 1606 (—NH2); 1672 (amide I); 1527, 1562, 1554 (amide II); 2926, 2853, 1468 (CH2); 1379, 2956, 2873 (Me).

Example 3

To a stirred solution of N-(2-Tetradecylhexadecanoyl)-15-amino-4,7,10,13-tetraoxapentadecanoic acid (general formula VIII; where $n_1$=3 and $n_5$=13; 206 mg, 0.29 mmol) in dry N,N-dimethylformamide (10 ml), bis(pentafluorophenyl) carbonate (128 mg, 0.32 mmol) and 4-methylmorpholine (0.25 ml, 2.45 mmol) were added and the stirring was continued at room temperature for 1 h. The reaction mixture was lyophilized from dioxane (2×20 ml) to give pentafluorophenyl ester of N-(2-Tetradecylhexadecanoyl)-15-amino-4,7,10,13-tetraoxapentadecanoic acid (251 mg), which was immediately used at the next condensation step.

The mixture of pentafluorophenyl ester of N-(2-Tetradecylhexadecanoyl)-15-amino-4,7,10,13-tetraoxapentadecanoic acid (181 mg; 0.21 mmol) and $N_2N_3N_4$-tri-(tert-butyloxycarbonyl)spermine (105 mg, 0.2 mmol) was dried in an apparatus equipped with septum for 4 h at room temperature and 0.1 Pa and then the apparatus was flushed with argon (2×). Dry N,N-dimethylformamide (8 ml) and N-ethyldiisopropylamine (0.5 ml) were added through the septum and the mixture was stirred at room temperature for 16 h. The flash chromatography of the crude reaction mixture on a silica gel column (150 ml) in toluene-ethyl acetate (gradient: 0-80% ethyl acetate, 10 ml/min, 160 min) afforded $N^1$—[N-(2-Tetradecylhexadecanoyl)-15-amino-4,7,10,13-tetraoxapentadecanoyl]-$N^4,N^9,N^{12}$-tri-tert-butoxycarbonyl-1,12-diamino-4,9-diazadodecane (general formula XI; X=aminopolyethyleneglycolcarboxamidic linker of the general formula II, where $n_1$=3 and Y=hydrophobic domain of the general formula V, where $n_5$=13; 124 mg, 50%). $^1$H NMR (400 MHz, CDCl$_3$) δ (ppm): 5.34-5.38 m, 1H (CH$_2$-6"); 3.75 t, J=6.06 Hz, 2H (CH$_2$-14); 3.60-3.68 m, 12H; 3.52-3.57 m, 2H; 3.43-3.50 m, 2H (8×CH$_2$O); 3.04-3.31 m, 12H (6×CH$_2$N); 2.48 t, J=5.87 Hz, 2H (CH$_2$-1); 2.00 tdd, J=9.25, 9.25, 5.18, 4.74 Hz, 1H (CH-2"); 1.76 s, 4H (CH$_2$-7, CH$_2$-8); 1.52-1.72 m, 4H (CH$_2$-3, CH$_2$-12); 1.41-1.51 m, 27H (tert-butyl); 1.18-1.34 m, 48H (CH$_2$-4'-15', CH$_2$-1"-13"'); 0.88 t, J=6.90 Hz, 6H (CH$_2$-16', CH$_2$-14"); $^{13}$C NMR (101 MHz, CDCl$_3$) δ (ppm): 176.10 (C-1"); 171.96 (C-1'); 155.74-156.20 3C (3×NCOO); 79.45-79.62 2C (2×C(CH$_3$)$_3$) 77.20 (C(CH$_3$)$_3$); 70.13-70.65 m 7C (7×CH$_2$—O); 67.35 (C-3'); 48.04 (C-2"); 46.37-46.97 m 4C (4×CH$_2$—N); 38.98 (C-15'); 37.01-37.24 m, 3C (C-2, C-2', C-1); 33.06 2C(C-3", C-1"'); 31.90 4C (C-5", C-14", C-3"', C-11"'); 29.21-29.97 m (CH$_2$-7"-12", CH$_2$-4"'-10"'); 28.45 m 9C (2×C(CH$_3$)$_3$) 27.63 2C (C-4", C-2"'); 22.67 (C-15", C-12"'); 14.09 (C-16", C-13", '); for $C_{66}H_{129}N_5O_{12}$ monoisotopic mass: calculated: 1184.0. found: MS ESI m/z: 1206.9 [M+Na]+. for $C_{66}H_{129}N_5O_{12}$—H+ HR-MS calculated: 1184.9711. found: 1184.9716; IR (CHCl$_3$): 1392, 1368, 1248, 1479, 1468, 1164 (tert-butyl); 3451, 3365, 1704, 1680, 1545, 1512, 1248 (C=O); 1671 (amide, amide II, C=O); 1122, 1095, 1042 (ether); 2928, 2856, 1468, 1442 (CH$_2$); 2960, 1456, 1380 (Me).

Example 4

Trifluoroacetic acid (2 ml; 26 mmol) was added to a solution of $N^1$—[N-(2-Tetradecylhexadecanoyl)-15-amino-4,7,10,13-tetraoxapentadecanoyl]-$N^4,N^9,N^{12}$-tri-tert-butoxycarbonyl-1,12-diamino-4,9-diazadodecane (general formula XI; X=aminopolyethyleneglycolcarboxamidic linker of the general formula II, where $n_1$=3 and Y=hydrophobic domain of the general formula V, where $n_5$=13; 83 mg, 0.07 mmol) in dichloromethane (5 ml) and the solution was stirred for 4 h at room temperature. The solution was evaporated in vacuo and the residue was lyophilized from dioxane (20 ml) to give $N^1$—[N-(2-Tetradecylhexadecanoyl)-15-amino-4,7,10,13-tetraoxapentadecanoyl]-1,12-diamino-4,9-diazadodecane (general formula I; X=aminopolyethyleneglycolcarboxamidic linker of the general formula II, where $n_1$=3 and Y=hydrophobic domain of the general formula V, where $n_5$=13; 61 mg). $^1$H NMR (400 MHz, methanol-d4) δ (ppm): 5.34-5.38 m, 1H (CH$_2$-6"); 3.75 t, J=5.94 Hz, 2H (CH$_2$-3'); 3.63 d, J=5.56 Hz, 2H; 3.53 t, J=5.60 Hz, 2H (7×CH$_2$—O); 3.33-3.39 m, 4H (CH$_2$-2); 2.99-3.19 m, 10H (6×CH$_2$N); 2.49 t, J=6.00 Hz, 2H (CH$_2$-2'); 2.18 tt, J=9.62, 4.85 Hz, 1H (CH$_2$-2"); 2.09 dt, J=15.16, 7.71 Hz, 2H (CH$_2$-3); 1.88 dt, J=13.50, 6.30 Hz, 2H 1.79-1.84 m, 4H (CH$_2$-7, CH$_2$-8, CH$_2$-12); 1.49-1.60 m, 4H (CH$_2$-3", CH$_2$-1"'); 1.29 s, 52H (CH$_2$-4"-15", CH$_2$-2"'-13"'); 0.87-0.93 m, 6H (CH$_2$-16", CH$_2$-14"'); $^{13}$C NMR (101 MHz, CDCl$_3$) δ (ppm): 172.68 (C-1"); 168.46 (C-1'); 73.77; 71.75; 71.63; 71.45 3C; 68.36; 58.63 (8×CH$_2$—O); 49.17; 48.97 2C; 48.90; (CH$_2$—N); 46.28 (C-2"); 38.02 (C-2); 37.78 (C-15'); 35.20 (C-2'); 34.28 (C-13); 33.19 (C-3); 30.92-30.71 m; 28.75; 27.85 (C-3"-14", C-1"'-12"', C-7, C-8); 25.58 (C-12); 24.45 2C (C-15", C-13"'); 23.85 (C-16", C-14"'); for $C_{51}H_{105}N_5O_6$ monoisotopic mass: calculated: 883.8. found: MS ESI m/z: 884.6 [M+H]+. for $C_{51}H_{105}N_5O_6$—H+ HR-MS calculated: 884.8138. found: 884.8128; IR (CHCl$_3$): 1604 (NH$_2$); 3316, 1182, 1136 (—NH—); 1674 (amide); 1560 (amide II); 1095, 836 (esters); 2927, 2855, 1476 (CH$_2$); 2960, 2870, 1378 (Me).

Example 5

The mixture of pentafluorophenyl ester 2-tetradecylhexadecanoic acid (general formula VII; where $n_5$=13; 164 mg, 0.26 mmol) and 15-amino-4,7,10,13-tetraoxapentadecanoic acid (49 mg, 0.079 mmol) was dried in an apparatus equipped with septum for 4 h at room temperature and 0.1 Pa. The apparatus was flushed with argon (2×) and then dry N,N-dimethylformamide (4 ml) and N-ethyldiisopropylamine (kolik?) were added through the septum and the mixture was stirred at room temperature for 16 h. Flash chromatography of the crude reaction mixture on silica gel column (150 ml) in toluene-ethyl acetate (gradient: 0-80% ethyl acetate, 10 ml/min, 160 min) gave N-(2-Tetradecyl hexadecanoyl)-15-amino-4,7,10,13-tetraoxapentadecanoic acid (general formula VIII, where $n_1$=3 and $n_5$=13; 174 mg; 94%). $^1$H NMR (400 MHz, CDCl$_3$) δ (ppm): 3.7 br. s., 16H 3.48 d, J=4.93 Hz, 2H (8×CH$_2$O); 2.53 t, J=5.49 Hz, 2H (CH$_2$-1); 2.13 br. s., 1H (CH-2'); 1.48-1.64 m, 2H 1.35-1.44 m, 2H (CH$_2$-3', CH$_2$-1"); 1.25 d, J=5.94 Hz, 42H (CH$_2$-4'-15', CH$_2$-1"-13"'); 0.81-0.95 m, 6H (CH$_2$-16', CH$_2$-14"); $^{13}$C NMR (101 MHz, CDCl$_3$) δ (ppm): 177.15 (C–1); 175.82 (C-1'); 69.91-70.72 m, 8C (8×CH$_2$—O); 48.28 (C-2'); 38.81 (C-15); 35.89 (C-2); 33.06 2C(C-3', C-1); 31.90 4C (C-5', C-14", C-3', C-11"); 29.21-29.97 m (CH$_2$-7'-12', CH$_2$-4"-10"'); 27.63 2C (C-4', C-2"'); 22.67 (C-15', C-12"); 14.09 (C-16', C-13"); for $C_{41}H_{81}NO_7$ monoisotopic mass: calculated: 699.6. found: MS ESI m/z: 722.7 [M+Na]+. for $C_{41}H_{81}NO_7$—Na+ HR-MS calculated: 722.5905. found: 722.5906; IR (CHCl$_3$): 1729 (COOH); 1122, 1097, 1402 (ether); 3450, 3345, 1579, 1516 (amide); 1658 (amide II); 2956, 2874, 1379 (Me); 2927, 2855, 1466, 1442 (CH$_2$).

Example 6

To a stirred solution of cholest-5-en-3β-yloxyacetic acid (general formula IX, where $n_2$=1; 134 mg, 0.3 mmol) in dry N,N-dimethylformamide (4 ml), bis(pentafluorophenyl) carbonate (130 mg, 0.33 mmol) and 4-methylmorpholine (0.1 ml, 1 mmol) were added and the mixture was stirred at room temperature for 1 h. The reaction mixture was lyophilized from dioxane (2×20 ml) to give pentafluorophenyl ester of cholest-5-en-3β-yloxyacetic acid (140 mg), which was immediately used at the next condensation step. The mixture of pentafluorophenyl ester of cholest-5-en-3β-yloxyacetic acid (140 mg; 0.23 mmol) and $N^2N^3N^4$-tri-(tert-butyloxycarbonyl)spermine (112 mg; 0.23 mmol) was dried in an apparatus equipped with septum for 4 h at room temperature and 0.1 Pa and the apparatus was flushed with argon (2×). Dry N,N-dimethylformamide (4 ml) and N-ethyldiisopropylamine (1 ml) were added through the septum and the mixture was stirred at room temperature for 16 h. Flash chromatography of the crude reaction mixture on a silica gel column (100 ml) in toluene-ethyl acetate (gradient: 0-40% of ethyl acetate, 10 ml/min, 160 min) gave $N^1$-(Cholest-5-en-3β-yloxy)acetyl-$N^4,N^9,N^{12}$-tri-tert-butoxycarbonyl-1,12-diamino-4,9-diazadodecane (general formula XI; where X=ω-hydroxyalkylcarboxyamidic linker of the general formula III, where $n_2$=1 and Y=hydrophobic domain of general formula VI; 178 mg; 86%). $^1$H NMR (400 MHz, CDCl$_3$) δ(ppm): 5.30-5.38 m, 1H (H-6"); 3.98 s, 2H (CH$_2$-2'); 3.02-3.35 m, 12H (6×CH$_2$N); 2.18-2.46 m, 2H (CH$_2$-4"); 1.37-1.51 m, 27H (terc-butyl); 1.01 s, 3H (CH$_3$-19"); 0.92 d, J=6.57 Hz, 3H (CH$_3$-21"); 0.88 d, J=1.77 Hz, 3H (CH$_3$-26"); 0.86 d, J=1.89 Hz, 3H (CH$_3$-27"); 0.80-2.06 m, 22H (cholesteryl); 0.68 s, 3H (CH$_3$-18"); $^{13}$C NMR (101 MHz, CDCl$_3$) δ(ppm): 176.15 (C-1'); 155.90-156.19 m, 3C (3×NCOO); 140.33 (C-5"); 120.94 (C-6"); 80.21 (C-3"); 79.56-79.59 m, 2C; (2×C (CH$_2$)$_3$); 77.20 (C(CH$_2$)$_3$); 67.61 (C-2'); 56.76 (C-14"); 56.19 (C-17"); 50.16 (C-9"); 46.41-46.96 m, 4C (C-4, C-6, C-9, C-11); 42.34 (C-13"); 40.18 (C-12"); 39.78 (C-24"); 39.52 (C-4"); 38.90 (C-2); 37.06 (C-1"); 36.82 (C-10"); 36.20 (C-22"); 35.78 (C-20"); 35.34 (C-13"); 31.94 (C-7"); 31.90 (C-8"); 28.4-28.51 m, 9C (3×C(CH$_2$)$_3$); 28.26 (C-2"); 28.21 (C-16"); 28.00 (C-25"); 25.82-26.18 m, 2C (C-7, C-8); 24.29 (C-15"); 23.83 (C-23"); 22.79 (C-26"); 22.54 (C-27"); 21.09 (C-11"); 19.37 (C-19"); 18.72 (C-21"); 11.86 (C-18"); for $C_{54}H_{96}N_4O_8$ monoisotopic mass: calculated: 928.7. found: MS ESI m/z: 929.3 [M+H]+. for $C_{54}H_{96}N_4O_8$ calculated: 69.79% C; 10.41% H; 6.03% N. found: 69, 60% C; 10, 64% H; 5.82% N. for $C_{54}H_{96}N_4O_8$—H+ HR-MS calculated: 929.7301. found: 929.7304; IR (CHCl$_3$): 1392, 1368, 1249, 2975, 1478, 1469, 1165, 865 (tert-butyl); 3454, 3421, 3356, 1705, 1680 (C=O); 1673, 1306 (amides+C=O); 2939, 1110 (ether); 2869, 1383, 1455, 1443 (Me); 1383, 1368 (C-26, C-27); [α]$_D$ 8.9° (c 0.259; CHCl$_3$).

Example 7

To a solution of $N^1$-(Cholest-5-en-3β-yloxy)acetyl-$N^4,N^9$,$N^{12}$-tri-tert-butoxycarbonyl-1,12-diamino-4,9-diazadodecane (general formula XI; where X=ω-hydroxyalkylcarboxyamidic linker of the general formula III, where $n_2$=1 and Y=hydrophobic domain of general formula VI; 148 mg, 0.16 mmol) in dichloromethane (5 ml), trifluoroacetic acid (2 ml, 26 mmol) was added and the solution was stirred for 4 h at room temperature. The solution was evaporated in vacuo and the residue was lyophilized from dioxane (20 ml) to afford $N^1$-(cholest-5-en-3β-yloxy)acetyl-1,12-diamino-4,9-diazadodecane (general formula I; where X=ω-hydroxyalkylcarboxyamidic linker of the general formula III, where $n_2$=1 and Y=hydrophobic domain of general formula VI; 100 mg; 100%). $^1$H NMR (400 MHz, methanol-d4) δ(ppm): 5.36-5.40 m, 1H (H-6"); 4.01 s, 2H (CH$_2$-2'); 3.37 t, J=6.51 Hz, 2H 3.24 tt, J=11.20, 4.60 Hz, 2H 2.96-3.17 m, 8H (6×CH$_2$N); 2.35-2.44 m, 1H (CH$_2$-4a"); 2.21-2.32 m, 1H (CH$_2$-4b"); 1.72-2.14 m, 13H (CH-1", H-12", H-2", H-7", H-16", CH$_2$-7, CH$_2$-7); 1.04 s, 3H (CH$_3$-19"); 0.95 d, J=6.57 Hz, 3H (CH$_3$-19"); 0.89 d, J=1.52 Hz, 3H (CH$_3$-19"); 0.87 d, J=1.39 Hz, 3H (CH$_3$-19"); 0.83-1.68 m, 16H (cholesteryl, CH$_2$-3, CH$_2$-9); 0.72 s, 3H (CH$_3$-19"); $^{13}$C NMR (101 MHz, methanol-d4) δ(ppm): 173.04 (C-1') 140.18 (C-5") 121.66 (C-6") 80.22 (C-3") 66.78 (C-2') 56.77 (C-17") 56.19 (C-17") 50.30 (C-9") 47.82 (C-10) 47.58 (C-6) 47.34 (C-3) 46.72 (C-8) 44.93 (C-12) 44.47 (C-1) 42.11 (C-13") 39.75 (C-12") 39.28 (C-24") 38.47 (C-4") 36.88 (C-1") 36.53 (C-10") 36.44 (C-22") 35.97 (C-11) 35.69 (C-7) 35.05 (C-8) 31.84 (C-7") 31.64 (C-8") 27.89 (C-2") 27.78 (C-16") 27.73 (C-25") 26.29 (C-2) 24.00 (C-15") 23.89 (C-23") 23.53 (C-12) 22.90 (C-26") 22.84 (C-27") 21.76 (C-11") 18.40 (C-19") 17.84 (C-21") 10.90 (C-18"); for $C_{39}H_{72}N_4O_2$ monoisotopic mass: calculated: 628.6. found: MS ESI m/z: 629.5 [M+H]+. for $C_{39}H_{72}N_4O_2$—H+ HR-MS calculated: 629.5728. found: 629.5715; IR (CHCl$_3$): 1694, 1670 (amide); 3312, 1533 (amide II); 3367, 1603 (NH2); 3312, 1165, 1138 (—NH—); 2947, 1111, 833 (ether); 1380, 1367 (C-26, C-27); 2960, 2868, 1380 (Me); 2844.1476 (CH2); [α]$_D$ 5°; (c 0.08; CHCl$_3$).

Example 8

To a stirred solution of 4-(cholest-5-en-3β-yloxy)butanoic acid (general formula IX; where $n_2$=3; 283 mg; 0.6 mmol) in dry N,N-dimethylformamide (4 ml), bis(pentafluorophenyl) carbonate (260 mg, 0.66 mmol) and 4-methylmorpholine (0.1 ml, 1 mmol) were added and the stirring was continued at room temperature for 1 h. The crude reaction mixture was lyophilized from dioxane (2×20 ml) to give pentafluorophenyl ester of 4-(cholest-5-en-3β-yloxy)butanoic acid (382 mg), which was immediately used at next reaction step.

The mixture of pentafluorophenyl ester of 4-(cholest-5-en-3β-yloxy)butanoic acid (216 mg, 0.34 mmol) and $N^2N^3N^4$-tri-(tert-butyloxycarbonyl)spermine (170 mg, 0.34 mmol) was dried in an apparatus equipped with septum for 4 h at room temperature and 0.1 Pa and then the apparatus was flushed with argon (2×). Dry N,N-dimethylformamide (4 ml) and N-ethyldiisopropylamine (1 ml) were added through the septum and the mixture was stirred at room temperature for 16 h. The crude reaction mixture was used in flash chromatography on silica gel column (100 ml) in toluene-ethyl acetate (gradient: 0-40% of ethyl acetate, 10 ml/min, 160 min) to give $N^1$-[(4-cholest-5-en-3β-yloxy)butanoyl]-$N^4,N^9$, $N^{12}$-tri-tert-butoxycarbonyl-4,9-diaza-1,12-diaminododecane (general formula XI; where X=ω-hydroxyalkylcarboxyamidic linker of the general formula III, where $n_2$=3 and Y=hydrophobic domain of general formula VI; 302 mg, 93%). $^1$H NMR (400 MHz, CDCl$_3$) δ(ppm): 5.32-5.35 m, 1H (H-6"); 3.50 t, J=6.32 Hz, 2H (CH$_2$-4'); 3.03-3.34 m, 12H (6×CH$_2$N); 2.31-2.39 m, 1H (H-4a"); 2.29 t, J=7.39 Hz, 2H (CH$_2$-2'); 2.12-2.23 m, 1H (H-4b"); 1.77-2.06 m, 7H (CH-1", H-12", H-2", H-7", H-16", CH$_2$-3'); 1.60-1.75 m, 8H (CH$_2$-3, CH$_2$-7, CH$_2$-8, CH$_2$-12); 1.43-1.47 m, 27H (tert-butyl); 1.00 s, 3H (CH$_3$-19"); 0.92 d, J=6.57 Hz, 3H (CH$_3$-21"); 0.88 d, J=1.77 Hz, 2H (CH3-26"); 0.86 d, J=1.77 Hz, 2H (CH$_3$-27"); 0.81-1.58 m, 17H (cholesteryl); 0.68 s, 2H (CH$_3$-18); $^{13}$C NMR (101 MHz, CDCl$_3$) δ (ppm): 172.82 (C-1') 156.06 br. s 3C (NCOO); 140.96 (C-5"); 121.51 (C-6"); 79.65 br. s 3C (3×C—CH$_3$); 79.02 (C-3"); 67.15 (C-4'); 56.80 (C-14"); 56.21 (C-17"); 50.24 (C-9"); 46.80 (C-6); 46.78 (C-4); 46.70 (C-9); 42.34 (C-13"); 39.82 (C-12"); 39.53 (C-4"); 39.19 (C-24"); 37.26 (C-1"); 36.90 (C-10"); 36.21 (C-22"); 35.78

(C-20"); 33.63 (C-2'); 31.96 (C-7"); 31.93 (C-8"); 28.49 (C-2"); 28.46 m 6C (6×CH3); 28.45 s 3C (3×CH₃); 28.37 (C-3); 28.22 s 2C(C-12; C-16"); 28.00 (C-25"); 26.16 br. s 3C (C-8; C-3; C-3'); 24.29 (C-15"); 23.83 (C-23"); 22.79 (C-26"); 22.55 (C-27"); 21.09 (C-11"); 19.38 (C-19"); 18.72 (C-21"); 11.86 (C-18"); for $C_{56}H_{100}N_4O_8$ monoisotopic mass: calculated: 956.7. found: MS ESI m/z: 957.4 [M+H]+. for $C_{56}H_{100}N_4O_8$—H+ HR-MS calculated: 957.7614. found: 957.7621; IR (CHCl₃): 1671 (amide); 1394, 1368, 1245 (tert-butyl) 3454, 1708, 1691 (C=O); 2930, 1134, 1110, 833 (ether); 1384, 1439 (Me); 1384, 1368 (C-26, C-27); 1179, 1348 (C—C(CH3)2); $[\alpha]_D$ −16.0° (c 0.075; CHCl₃).

Example 9

Trifluoroacetic acid (1 ml; 13 mmol) was added to a solution of $N^1$-[(4-cholest-5-en-3β-yloxy)butanoyl]-$N^4,N^9,N^{12}$-tri-tert-butyloxycarbonyl-4,9-diaza-1,12-diaminododecane (general formula XI; where X=ω-hydroxyalkylcarboxyamidic linker of the general formula III, where $n_2$=3 and Y=hydrophobic domain of general formula VI; 259 mg, 0.27 mmol) in dichloromethane (5 ml) and the solution was stirred for 4 h at room temperature. The solution was evaporated and the residue was lyophilized from dioxane (20 ml) to give 175 mg of $N^1$-[4-(cholest-5-en-3β-yloxy)butanoyl]-1,12-diamino-4,9-diazadodecane (general formula I; where X=ω-hydroxyalkylcarboxyamidic linker of the general formula III, where $n_2$=3 and Y=hydrophobic domain of general formula VI). ¹H NMR (400 MHz, MeOD-d4) δ(ppm): 5.35-5.39 m, 1H (CH-6"); 3.52 t, J=6.25 Hz, 2H (CH₂-4); 2.97-3.20 m, 12H (6×CH₂—NH); 2.38 dd, J=4.74, 1.83 Hz, 1H (CH-4a"); 2.32 t, J=7.40 Hz, 2H (CH₂-2'); 1.96-2.22 m, 7H (cholesteryl); 1.75-1.95 m, 14H (CH₂-3; CH₂-7; CH₂-8; CH₂-7; CH₂-12; CH₂-3'; CH₂-2"); 1.04 s, 3H (CH₃-19"); 0.96 d, J=6.57 Hz, 3H (CH₃-21"); 0.93-1.67 m, 29H (cholesteryl); 0.91 d, J=1.52 Hz, 3H (CH₃-26"); 0.89 d, J=1.52 Hz, 3H (CH₃-27"); 0.74 s, 3H (CH₃-18"); ¹³C NMR (101 MHz, MeOD-d4) δ(ppm): 177.23 (C-1'); 142.09 (C-5"); 119.77 (C-6"); 80.71 (C-3); 68.31 (C-4'); 58.33 (C-14"); 57.75 (C-17"); 51.89 (C-11); 49.78 (C-9"); 48.26 (C-4); 46.50 (C-6); 46.00 (C-9); 43.65 (C-13"); 41.31 (C-13); 40.83 (C-12"); 40.38 (C-4"); 38.58 (C-25"); 38.12 (C-1"); 37.98 (C-9"); 37.53 (C-22"); 37.24 (C-2); 36.98 (C-20"); 33.93 (C-12); 33.70 (C-2'); 33.40 (C-7"); 33.19 (C-8"); 29.66 (C-7); 29.44 (C-8); 29.27 (C-2"); 27.83 (C-16"); 27.49 (C-25"); 25.50 (C-3'); 25.45 (C-3); 25.09 (C-15"); 24.36 (C-23"); 23.32 (C-26"); 23.08 (C-27"); 22.33 (C-11"); 19.99 (C-19"); 19.41 (C-21"); 12.47 (C-18"); for $C_{41}H_{76}N_4O_2$ monoisotopic mass: calculated 656.6. found: MS ESI m/z: 679.6 [M+Na]+. for $C_{41}H_{76}N_4O_2$—Na+ HR-MS calculated: 679.6017. found: 679.6042; IR (CHCl₃): 1669 (amide I); 1559 (amide II); 3305, 1603, 1179, 1139 (—NH₂, —NH—); 1383, 1367 (C-26, C-27); 2953, 2869, 1383, 1445 (Me); 2935, 1117, 1100 (ether); $[\alpha]_D$ −13° (c 0.146; CHCl₃).

Example 10

To a stirred solution of (cholest-5-en-3β-yloxy)acetyl-15-amino-4,7,10,13-tetraoxapentadecanoic acid (general formula X; where $n_3$=1 and $n_4$=3; 149 mg, 0.22 mmol) in dry N,N-dimethylformamide (5 ml), bis(pentafluorophenyl) carbonate (100 mg, 0.39 mmol) and 4-methylmorpholine (0.25 ml; 2.45 mmol) were added and the mixture was stirred at room temperature for 1 h. The reaction mixture was lyophilized from dioxane (2×20 ml) to give pentafluorophenyl ester of (cholest-5-en-3β-yloxy)acetyl-15-amino-4,7,10,13-tetraoxapentadecanoyl acid (140 mg), which was immediately used in the next condensation step.

The mixture of pentafluorophenyl ester of (cholest-5-en-3β-yloxy)acetyl-15-amino-4,7,10,13-tetraoxapentadecanoyl acid (140 mg; 0.23 mmol) and $N^2N^3N^4$-tri-(tert-butyloxycarbonyl)spermine (170 mg; 0.34 mmol) was dried in an apparatus equipped with septum for 1 h at room temperature and 0.1 Pa and the apparatus was flushed with argon (2×). Dry N,N-dimethylformamide (8 ml) and N-ethyldiisopropylamine (0.5 ml) were added through the septum and the mixture was stirred at room temperature for 12 h. Flash chromatography of the crude reaction mixture on a silica gel column (100 ml) in toluene-ethyl acetate (gradient: 0-40% of ethyl acetate, 10 ml/min, 160 min) gave $N^1$-[(Cholest-5-en-3β-yloxy)acetyl-15-amino-4,7,10,13-tetraoxapentadecanoyl]-$N^4,N^9,N^{12}$-tri-tert-butoxycarbonyl-1,12-diamino-4,9-diazadodecane (general formula XI; where X=ω-hydroxyalkylcarboxamidopolyethyleneglycolcarboxyamidic linker of the general formula IV, where $n_3$=1 and $n_4$=3; Y=hydrophobic domain of general formula VI; 50 mg; 19%). ¹H NMR (400 MHz, CDCl₃) δ ppm: 5.36 d, J=5.05 Hz, 1H (CH₂-5"); 3.98 s, 2H (CH₂COO); 3.72-3.77 m, 2H (CH₂-3"); 3.64 d, J=4.04 Hz, 12H (6×CH₂O); 3.58 t, J=4.90 Hz, 3H (CH₂O); 3.50 q, J=5.50 Hz, 2H (CH₂-14'); 3.05-3.30 m, 13H (6×CH₂N); 2.48 t, J=5.94 Hz, 2H (CH₂-2'); 2.31-2.38 m, 1H (CH-4"a); 2.18-2.28 m, 1H (CH-4"b); 1.76-2.06 m, 6H (cholesteryl); 1.61-1.73 m, 4H (CH₂-3, CH₂-7, CH₂-8, CH₂-12); 1.41-1.51 m, 27H (tert-butyl); 1.01 s, 3H (CH₃-19"); 0.94-1.41 m, 17H (cholesteryl); 0.92 d, J=6.57 Hz, 3H (CH₃-21"); 0.87 d, J=1.77 Hz, 3H (CH₃-26"); 0.86 d, J=1.77 Hz, 3H (CH₃-27"); 0.68 s, 3H (CH₃-18"); for $C_{65}H_{117}N_5O_{13}$—H HR-MS monoisotopic mass: calculated: 1176.87206. found: 1176.87174.

Example 11

To a solution of $N^1$-[(Cholest-5-en-3β-yloxy)acetyl-15-amino-4,7,10,13-tetraoxapentadecanoyl]-$N^4,N^9,N^{12}$-tri-tert-butoxycarbonyl-1,12-diamino-4,9-diazadodecane (general formula XI; where X=ω-hydroxyalkylcarboxamidopolyethyleneglycolcarboxyamidic linker of the general formula IV, where $n_3$=1 and $n_4$=3; Y=hydrophobic domain of general formula VI; 51 mg, 0.04 mmol) in dichloromethane (5 ml) trifluoroacetic acid (1 ml, 13 mmol) was added and the solution was stirred for 4 h at room temperature. The solution was evaporated in vacuo and the residue was lyophilized from dioxane (20 ml) to afford $N^1$-[(Cholest-5-en-3β-yloxy)acetyl-15-amino-4,7,10,13-tetraoxapentadecanoyl]-1,12-diamino-4,9-diazadodecane (general formula I, where X=ω-hydroxyalkylcarboxamidopolyethyleneglycolcarboxyamidic linker of the general formula IV, where $n_3$=1 and $n_4$=3; Y=hydrophobic domain of general formula VI; 32 mg, 84%). ¹H NMR (400 MHz, CDCl₃) δ ppm: 5.32 br. s., 2H (CH₂-6"); 3.73-3.86 m, 2H; 3.54-3.72 m, 14H; 3.48-3.54 m, 21-1 (8×CH₂—O, PEG); 3.26-3.47 m, 10H; 3.11-3.25 m, 2H; 2.87-3.09 m, 2H (6×CH₂—N, spermine; CH₂—N, PEG); 2.54 t, J=8.20 Hz, 2H (CH₂-4"); 2.24-2.47 m, 4H (CH₂-2', CH₂-2 yloxy acetyl); 1.99-2.14 m, 8H (cholesteryl); 1.76-1.99 m, 8H (4×CH₂-spermine); 1.55 dt, J=13.1, 6.28 Hz, 15H (CH₂-3, butanoyl); 0.84-1.43 m, 37H (cholesteryl); 1.018 s 3H (CH₃-19"); 0.93 d, J=6.2 Hz, 3H (CH₃-21"); 0.91 d, J=1.50 Hz, 3H (CH₃-26"); 0.87 d, J=1.28 Hz, 3H (CH₃-27"); 0.69 s, 3H (CH₃-18"); for $C_{50}H_{93}N_5O_7$—H HR-MS, calculated m/z: 876.71478. found m/z: 876.71418.

Example 12

To a stirred solution of [4-(Cholest-5-en-3β-yloxy)butanoyl]-15-amino-4,7,10,13-tetraoxapentadecanic acid (general formula X, where $n_3=3$ and $n_4=3$; 117 mg, 0.17 mmol) in dry N,N-dimethylformamide (5 ml), bis(pentafluorophenyl) carbonate (73 mg, 0.18 mmol) and 4-methylmorpholine (0.1 ml; 1 mmol) were added and the mixture was stirred at room temperature for 1 h. The reaction mixture was lyophilized from dioxane (2×20 ml) to give pentafluorophenyl ester of [4-(Cholest-5-en-3β-yloxy)butanoyl]-15-amino-4,7,10,13-tetraoxapentadecanoic acid (184 mg), which was immediately used in the next condensation step.

The mixture of pentafluorophenyl ester of [4-(Cholest-5-en-3β-yloxy)butanoyl]-15-amino-4,7,10,13-tetraoxapentadecanoc acid (80 mg; 0.09 mmol) and $N^2N^3N^4$-tri-(tert-butyloxycarbonyl)spermine (60 mg; 0.11 mmol) was dried in an apparatus equipped with septum for 1 h at room temperature and 0.1 Pa and the apparatus was flushed with argon (2×). Dry N,N-dimethylformamide (4 ml) and N-ethyldiisopropylamine (1 ml) were added through the septum and the mixture was stirred at room temperature for 12 h. Flash chromatography of the crude reaction mixture on a silica gel column (100 ml) in toluene-ethyl acetate (gradient: 0-40% of ethyl acetate, 10 ml/min, 160 min) gave N'-{[4-(Cholest-5-en-3β-yloxy)butanoyl]-15-amino-4,7,10,13-tetraoxapentadecanoyl}-$N^4,N^9,N^{12}$-tri-tert-butoxycarbonyl-1,12-diamino-4,9-diazadodecane (general formula XI, where X=ω-hydroxyalkylcarboxamidopolyethyleneglycolcarboxyamidic linker of the general formula IV, where $n_3=3$ and $n_4=3$; Y=hydrophobic domain of general formula VI; 50 mg; 19%). $^1$H NMR (400 MHz, CDCl$_3$) δ ppm: 5.34-5.38 m, 1H (CH$_2$-6"); 3.74 t, J=6.10 Hz, 2H (CH$_2$-3); 3.58-3.66 m, 14H (7×CH$_2$—O); 3.53-3.57 m, 2H (CH$_2$-14); 3.50 td, J=6.20, 0.90 Hz, 1H (CH$_2$-4'); 3.44 q, J=5.05 Hz, 1H (CH-3"); 3.04-3.30 m, 12H (CH$_2$—N); 2.48 t, J=6.06 Hz, 1H (CH$_2$-2); 2.34 ddd, J=13.20, 4.70, 2.10 Hz, 1H (H-4a"); 2.29 t, J=7.39 Hz, 2H (CH$_2$-2'); 1.76-2.25 m, 13H (cholesteryl); 1.60-1.75 m, 8H (CH$_2$-3, CH$_2$-7, CH$_2$-8, CH$_2$-12); 1.41-1.47 m, 27H (terc-butyl); 0.99 s, 3H (CH$_3$-19"); 0.92 d, J=6.57 Hz, 3H (CH$_3$-21"); 0.87 d, J=1.77 Hz, 3H (CH$_3$-26"); 0.86 d, J=1.77 Hz, 3H (CH$_3$-27"); 0.84-1.57 m, 33H (cholesteryl); 0.68 s, 3H (CH$_3$-18"); for C$_{67}$H$_{121}$N$_5$O$_{13}$—H HR-MS, calculated m/z: 1204.90337. found m/z: 1204.90298.

Example 13

To a solution of $N^1$-{[4-(Cholest-5-en-3β-yloxy)butanoyl]-15-amino-4,7,10,13-tetraoxapentadecanoyl}-$N^4,N^9,N^{12}$-tri-tert-butoxycarbonyl-1,12-di amino-4,9-diazadodecane (general formula XI, where X=ω-hydroxyalkylcarboxamidopolyethyleneglycolcarboxyamidic linker of the general formula IV, where $n_3=3$ and $n_4=3$; Y=hydrophobic domain of general formula VI; 83 mg, 0.07 mmol) in dichloromethane (5 ml) trifluoroacetic acid (2 ml, 26 mmol) was added and the solution was stirred for 4 h at room temperature. The solution was evaporated in vacuo and the residue was lyophilized from dioxane (20 ml) to afford $N^1$-{[4-(Cholest-5-en-3β-yloxy)butanoyl]-15-amino-4,7,10,13-tetraoxapentadecanoyl}-1,12-diamino-4,9-diazadodecane (general formula I, where X=ω-hydroxyalkylcarboxamidopolyethyleneglycolcarboxyamidic linker of the general formula IV, where $n_3=3$ and $n_4=3$; Y=hydrophobic domain of general formula VI; 61 mg; 98%). $^1$H NMR (400 MHz, CDCl$_3$) δ ppm: 5.36 br. s., 2H (CH$_2$-6"); 3.73-3.85 m, 2H; 3.54-3.72 m 14H; 3.46-3.54 m, 2H (8×CH$_2$—O, PEG); 3.58 t, J=6.57 Hz (CH$_2$-4, butanoyl); 3.26-3.46 m, 10H; 3.10-3.24 m, 2H; 2.87-3.09 m s, 2H (6×CH$_2$—N, spermine; CH$_2$—N, PEG); 2.54 t, J=8.20 Hz, 2H (CH$_2$-4"); 2.24-2.47 m, 4H (CH$_2$-2', CH$_2$-3 butanoyl); 1.99-2.14 m, 8H (cholesteryl); 1.76-1.99 m, 8H (4×CH$_2$-spermine); 1.55 dt, J=13.07, 6.22 Hz, 15H (CH$_2$-3, butanoyl); 0.84-1.43 m, 37H (cholesteryl); 1.018 s, 3H (CH$_3$-19"); 0.945 d, J=6.6 Hz, 3H (CH$_3$-21"); 0.90 d, J=1.52 Hz, 3H (CH$_3$-26"); 0.89 d, J=1.26 Hz, 3H (CH$_3$-27"); 0.71 s, 3H (CH$_3$-18"); for C$_{52}$H$_{97}$N$_5$O$_7$—H HR-MS, calculated m/z: 904.74608. found m/z: 904.74595.

Example 14

To a stirred 60% suspension of NaH in mineral oil (400 mg; 3 mmol) under nitrogen a solution of cholesterol (387 mg, 1 mmol) in dry tetrahydrofuran (30 ml) and tert-butyl bromoacetate (585 mg; 3 mmol) was slowly added and the mixture was refluxed under stirring for 16 h. After cooling to room temperature, water (50 ml) was carefully added and the product was taken in diethyl ether (2×50 ml). The combined extracts were dried over anhydrous MgSO$_4$, and concentrated in vacuo. Flash chromatography of the residue on silica gel column (200 ml) in hexane-tert-butyl methyl ether (gradient: 0-30%—tert-butyl methyl ether, 10 ml/min, 160 min) afforded compound tert-Butyl cholest-5-en-3β-yloxyacetate (general formula XII, where $n_2=1$; 131 mg, 26%). $^1$H NMR (400 MHz, CDCl$_3$) δ (ppm): 5.34-5.38 m, 1H (H-6); 4.01 s, 2H (H-1'); 3.24 tt, J=11.23, 4.56 Hz, 1H (H-3); 2.37-2.43 m, 1H (H-4a); 2.22-2.32 m, 1H (H-4b); 1.76-2.07 m, 5H (CH-1, H-12, H-2, H-7, H-16); 1.48 s, 9H (t-butyl); 1.01 s, 3H (CH$_3$-19); 0.92 d, J=6.60 Hz, 3H (CH$_3$-21); 0.88 d, J=1.80 Hz, 3H (CH$_3$-26); 0.86 d, J=1.80 Hz, 3H (CH$_3$-27); 0.83-1.63 m, 42H (cholesterol+tert-butyl) 0.68 s, 3H (CH$_3$-18); $^{13}$C NMR (101 MHz, CDCl$_3$) δ (ppm): 170.11 (C-2') 140.69 (C-5) 121.78 (C-6) 81.33 (CCH$_3$) 79.81 (C-3) 66.11 (C-1') 56.80 (C-14) 56.20 (C-17) 50.20 (C-9) 42.35 (C-13) 39.81 (C-12) 39.53 (C-24) 38.79 (C-4) 37.17 (C−1) 36.85 (C-10) 36.21 (C-22) 35.78 (C-20) 31.95 (C-7) 31.92 (C-8) 28.22 (C-2) 28.16 (C-16) 28.12 3C (3×CCH$_3$) 28.00 (C-25) 24.29 (C-15) 23.84 (C-23) 22.80 (C-26) 22.55 (C-27) 21.08 (C-11) 19.35 (C-19) 18.72 (C-21) 11.86 (C-18); for C$_{33}$H$_{56}$O$_3$ monoisotopic mass: calculated: 500.4. found: MS ESI m/z: 524.0 [M+Na]+. for C$_{33}$H$_{56}$O$_3$—Na+ HR-MS calculated: 523.41217. found: 523.41201; IR (CHCl$_3$): 2954, 2869, 1467, 1457, 1370, 1394, 1161, 1032, 843 (tert-butyl); 1744, 1712, 1125 (C═O); 1670 (C═C); 1125 (C—O); 1181, 1370 (C-26, C-27); 1125 (ether); [α]$_D$ −33.7° (c 0.338; CHCl$_3$).

Example 15

To a solution of tert-Butyl cholest-5-en-3β-yloxyacetate (general formula XII, where $n_2=1$; 111 mg, 0.22 mmol) in diethyl ether (8 ml) formic acid (5 ml, 132 mmol) was added and the solution was stirred at 64° C. for 5 h. The solvents were evaporated in vacuo and the residue was lyophilized from dioxane (20 ml) to afford Cholest-5-en-3β-yloxyacetic acid (general formula IX, where $n_2=1$; 99 mg, 100%). $^1$H NMR (400 MHz, CDCl$_3$) δ (ppm): 5.33-5.41 m, 1H (H-6); 4.16 s, 2H (H-1'); 3.31 tt, J=11.20, 4.60 Hz, 1H (H-3); 2.35-2.43 m, 1H (H-4a); 2.23-2.33 m, 1H (H-4b); 1.76-2.07 m, 5H (CH-1, H-12, H-2, H-7, H-16); 1.01 s, 3H (CH$_3$-19); 0.92 d, J=6.57 Hz, 3H (CH$_3$-21); 0.88 d, J=1.77 Hz, 3H (CH$_3$-26); 0.86 d, J=1.64 Hz, 3H (CH$_3$-27); 0.79-1.67 m, 33H (cholesteryl); 0.68 s, 3H (CH$_3$-18); $^{13}$C NMR (101 MHz, CDCl$_3$) δ (ppm): 172.98 (C-2') 139.88 (C-5) 122.45 (C-6) 80.49 (C-1) 65.20 (C-1') 56.72 (C-14) 56.15 (C-17) 50.10 (C-9) 42.31 (C-13) 39.73 (C-12) 39.51 (C-24) 38.69 (C-4) 36.96 (C-1) 36.76 (C-10) 36.18 (C-22) 35.78 (C-20) 31.91 (C-7) 31.85 (C-8) 28.21 (C-2) 28.10 (C-16) 28.01 (C-25) 24.27 (C-15) 23.82 (C-23) 22.81 (C-26) 22.55 (C-27) 21.06 (C-11) 19.32 (C-19) 18.71 (C-21) 11.86 (C-18); for C$_{29}$H$_{48}$O$_3$ monoisotopic mass: calculated: 444.4. found: MS ESI m/z: 467.9

[M+Na]+. for $C_{29}H_{48}O_3$—Na+ HR-MS calculated: 467.3496. found: 467.3496; IR ($CHCl_3$): 3517, 1783, 1731, 1287 (COOH); 1133, 1110, 1087, 1070, 842 (ether); 1668, 1334 (C=C); 1381, 1367, 1170 (i-propyl); 2954, 2869, 1443, 1367 (Me); $[\alpha]_D$ –16.1° (c 0.031; $CHCl_3$).

Example 16

To a solution of Cholest-5-en-3β-yloxyacetic acid (general formula IX, where $n_2$=1; 160 mg, 0.36 mmol) in dry N,N-dimethylformamide (5 ml) bis(pentafluorophenyl) carbonate (156 mg, 0.39 mmol) and 4-methylmorpholine (0.25 ml, 2.45 mmol) were added. The mixture was stirred at room temperature for 1 h and then lyophilized from dioxane (2×50 ml) to give pentafluorophenyl ester of Cholest-5-en-3β-yloxyacetic acid (164 mg), which was immediately used in the next reaction step.

The mixture of pentafluorophenyl ester of Cholest-5-en-3β-yloxyacetic acid (175 mg, 0.29 mmol) and 15-amino-4,7,10,13-tetraoxapentadecanoic acid (160 mg, 0.60 mmol) was dried in an apparatus equipped with septum for 4 h at room temperature and 0.1 Pa. The apparatus was flushed with argon (2×) and then dry N,N-dimethylformamide (6 ml) and N-ethyldiisopropylamine (2 ml) were added through the septum and the mixture was stirred at room temperature for 16 h. Flash chromatography of the crude reaction mixture on silica gel column (200 ml) in toluene-ethyl acetate (gradient: 0-80% ethyl acetate, 10 ml/min, 160 min) gave (cholest-5-en-3β-yloxy)acetyl-15-amino-4,7,10,13-tetraoxapentadecanol acid (general formula X, where $n_3$=1 and $n_4$=3; 167 mg, 84%). For $C_{40}H_{69}NO_8Na$ HR-MS, calculated: m/z: 714.4915. found: m/z: 714.4916; $^1H$ NMR (400 MHz, $CDCl_3$) δ ppm: 5.34-5.38 m, 1H ($CH_2$-5'); 4.00 s, 2H ($CH_2COO$); 3.78 t, J=6.06 Hz, 2H ($CH_2$-3); 3.59-3.68 m, 14H (7×$CH_2O$); 3.52 q, J=5.47 Hz, 2H ($CH_2$-14); 3.23 tt, J=11.24, 4.36 Hz, 1H (CH-3'); 2.61 t, J=6.00 Hz, 2H ($CH_2$-2); 2.36 ddd, J=13.20, 4.70 (CH-4'a); 2.19-2.29 m, 1H (CH-4'b); 1.77-2.06 m, 5H (cholesteryl); 1.00 s, 3H ($CH_3$-19'); 1.29 d, J=3.66 Hz, 24H (cholesteryl); 0.92 d, J=6.57 Hz, 3H ($CH_3$-21'); 0.88 d, J=1.89 Hz, 3H ($CH_3$-26'); 0.86 d, J=1.77 Hz, 3H ($CH_3$-27'); 0.68 s, 3H ($CH_3$-18').

Example 17

A solution of cholesteryl tosylate (2.8 g, 5.1 mmol) and 4-hydroxybutanenitrile (0.61 g, 7.1 mmol) in toluene was stirred at 120° C. for 24 h and then the solvent was evaporated in vacuo. The obtained crude 4-(cholest-5-en-3β-yloxy)butanenitrile was dissolved in isopropyl alcohol (30 ml), aqueous NaOH (12%; 100 ml) was added and the mixture was stirred at 100° C. for 3 days. The mixture was cooled to room temperature, aqueous hydrochloric acid (10%, 100 ml) was added and the product was taken in diethyl ether (4×30 ml). The combined extracts were dried over anhydrous $MgSO_4$ and concentrated in vacuo. Flash chromatography of the residue on silica gel column (320 ml) in toluene-ethyl acetate (gradient: 0-40% ethyl acetate, 10 ml/min, 160 min) afforded 4-(Cholest-5-en-3β-yloxy)butanoic acid (general formula IX, where $n_2$=3; 345 mg, 10%). $^1H$ NMR (400 MHz, $CHCl_3$) δ (ppm): 5.32-5.39 m, 1H (H-6); 3.55 td, J=5.90, 1.40 Hz, 2H (CH2-1'); 3.17 tt, J=11.21, 4.39 Hz, 1H (H-3); 2.49 t, J=7.01 Hz, 2H (CH2-3'); 2.36 ddd, J=13.17, 4.71, 2.08 Hz, 1H (H-4a); 2.14-2.24 m, 1H (H-4b); 1.93-2.05 m, 2H (CH2-1, H-12); 1.90 t, J=6.20 Hz, 2H (CH2-2'); 1.78-1.88 m, 3H (H-2, H-7, H-16); 1.02-1.63 m, 22H (cholesteryl); 1.01 s, 3H (CH3-19); 0.92 d, J=6.57 Hz, 3H (CH3-21); 0.88 d, J=1.77 Hz, 3H (CH3-26); 0.86 d, J=1.77 Hz, 3H (CH3-27); 0.68 s, 3H (CH3-18); $^{13}C$ NMR (101 MHz, $CHCl_3$) δ (ppm): 178.28 (C-1') 140.76 (C-5) 121.69 (C-6) 79.31 (C-3) 66.88 (C-4') 56.77 (C-14) 56.16 (C-17) 50.18 (C-9) 42.31 (C-13) 39.78 (C-12) 39.51 (C-24) 38.98 (C-4) 37.18 (C-1) 36.86 (C-10) 36.18 (C-22) 35.78 (C-20) 31.94 (C-7) 31.88 (C-8) 31.37 (C-2') 28.29 (C-2) 28.23 (C-16) 28.01 (C-25) 25.06 (C-3') 24.28 (C-15) 23.83 (C-23) 22.81 (C-26) 22.55 (C-27) 21.06 (C-11) 19.36 (C-19) 18.71 (C-21) 11.86 (C-18); for $C_{31}H_{52}O_3$ monoisotopic mass: calculated: 472.4. found: MS ESI m/z: 495.4 [M+Na]+. for $C_{31}H_{52}O_3$ calculated: 78.76% C; 11.09% H. found: 78.80% C; 11.18% H; IR ($CHCl_3$): 3517, 2718, 1741, 1710, 1415, 1285 (COOH); 1134, 1105, 1070, 1083, 841 (ether); 1670, 1334 (C=C); 2954, 2869, 1445, 1366 (Me); $[\alpha]_D$-27.2° (c 0.136; $CHCl_3$).

Example 18

To a solution of 4-(Cholest-5-en-3β-yloxy)butanoic acid (general formula IX, where $n_2$=3; 283 mg, 0.6 mmol) in dry N,N-dimethylformamide (4 ml) bis(pentafluorophenyl) carbonate (260 mg, 0.66 mmol) and 4-methylmorpholine (0.1 ml, 1 mmol) were added. The mixture was stirred at room temperature for 1 h and then lyophilized from dioxane (2×20 ml) to give pentafluorophenyl ester of 4-(Cholest-5-en-3β-yloxy)butanoic acid (382 mg), which was immediately used in the next reaction step.

The mixture of pentafluorophenyl ester of 4-(Cholest-5-en-3β-yloxy)butanoic acid (121 mg, 0.19 mmol) and 15-amino-4,7,10,13-tetraoxapentadecanoic acid (104 mg, 0.39 mmol) was dried in an apparatus equipped with septum for 4 h at room temperature and 0.1 Pa. The apparatus was flushed with argon (2×) and then dry N,N-dimethylformamide (4 ml) and N-ethyldiisopropylamine (1 ml) were added through the septum and the mixture was stirred at room temperature for 16 h. Flash chromatography of the crude reaction mixture on silica gel column (100 ml) in toluene-ethyl acetate (gradient: 0-40% ethyl acetate, 10 ml/min, 160 min) gave [4-(Cholest-5-en-3β-yloxy)butanoyl]-15-amino-4,7,10,13-tetraoxapentadecanol acid (general formula X, where $n_3$=3 and $n_4$=3; 208 mg, 88%). $^1H$ NMR (400 MHz, Acetone) δ ppm: 3.71 t, J=6.32 Hz, 2H ($CH_2$-3); 3.55-3.60 m, 14H (7×$CH_2$—O); 3.51 t, J=5.60 Hz, 2H ($CH_2$-14); 3.45 t, J=6.32 Hz, 2H ($CH_2$-4'); 3.34 q, J=5.73 Hz, 1H (CH-3"); 2.53 t, J=6.32 Hz, 2H ($CH_2$-2); 2.34 ddd, J=13.20, 4.70, 2.10 Hz, 1H (H-4a"); 2.24 t, J=7.45 Hz, 2H ($CH_2$-2'); 1.82-2.17 m, 5H (cholesteryl); 1.76-1.82 m, 2H ($CH_2$-3'); 1.01 s, 3H ($CH_3$-19"); 0.94 d, J=6.57 Hz, 3H ($CH_3$-21"); 0.87 d, J=1.26 Hz, 3H ($CH_3$-26"); 0.86 d, J=1.52 Hz, 3H ($CH_3$-27"); 0.81-1.66 m, 34H (cholesteryl); 0.71 s, 3H ($CH_3$-18"); for $C_{42}H_{73}NO_8$—H HR-MS, calculated m/z: 720.5409. found m/z: 720.5407.

Biological Activities

Example 19

Encapsulation of Anionic Antiviral Drugs into Cationic Liposomes and Enhancement of the In Vitro Antiviral Effect Methods:

The liposomes were prepared by standard procedures, e.g. by the hydration of a lipid film followed by the extrusion of the liposomes through a polycarbonate filter Nucleopore of the 100-nm pore size. The size and zeta-potential was measured using the instrument Nanosizer ZS (Malvern).

After the separation of liposomes from free Cidofovir® [(S)-1-(3-hydroxy-2-phosphonylmethoxypropyl)cytosine]

by ultracentrifugation and lysis of the liposomes by 20 mM cholic acid, the concentration of the encapsulated nucleotide antiviral drug was determined by spectrophotometry. The UV absorbance was measured at 272 nm (the molar extinction coefficient c=9000, pH=7.0).

Figure 2A:
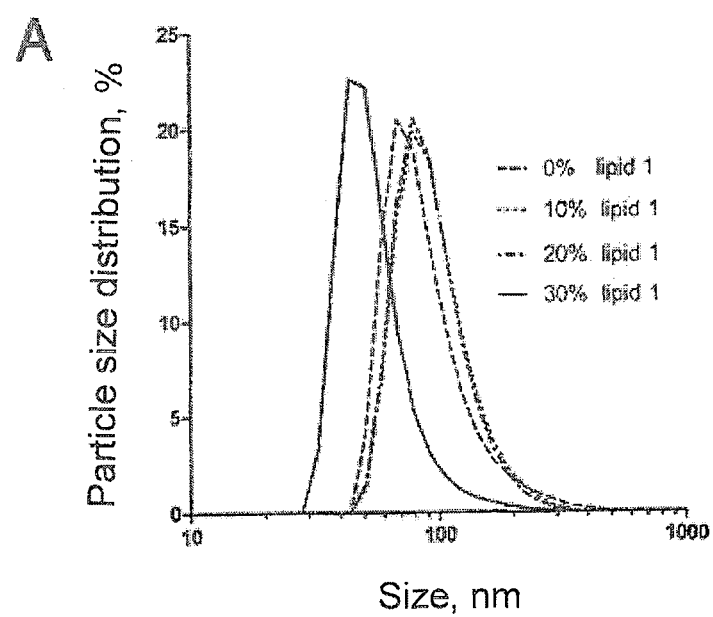
FIG. 2 A,B: Size distribution of liposomes (A) and distribution of zeta-potential of liposomes (B) with 0, 10, 20, and 30 mol. % content of lipid 1, respectively.
Figure 2B:
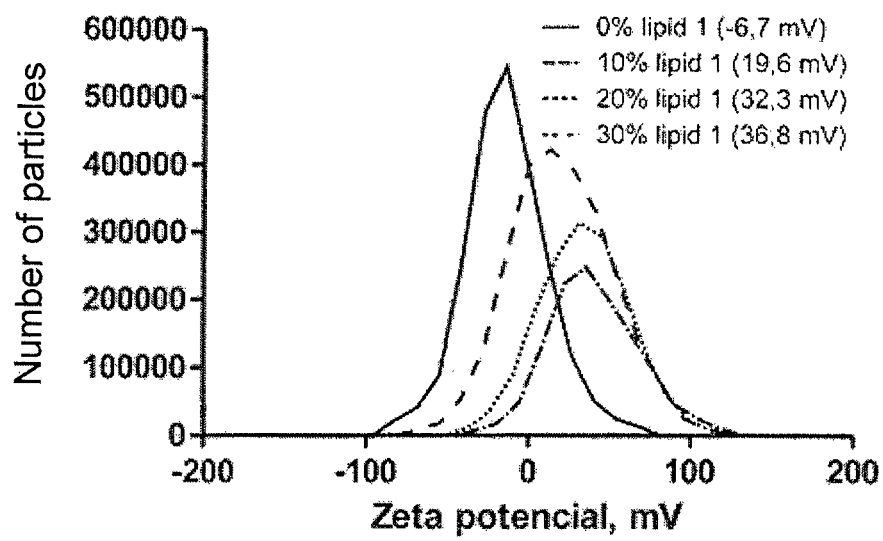

Results:

The cationic lipids 1-6 together with auxiliary lipids (e.g. EPC, i.e. egg phosphatidyl choline) are capable of forming stable lipid bilayers and therefore, they can be used in the preparation of liposomes, as shown in FIG. 1. The size of the liposomes corresponds to the size of the filter used for the extrusion (as demonstrated by FIG. 2 for the lipid 1). The zeta-potential of the liposomes depends on the ratio: cationic lipid/total lipid. In the PBS solution of a neutral pH value, at 20-30 mol. % of the cationic lipid in the lipid mixture, the zeta-potential reaches values above 30 mV. The influence of the liposomal cationic lipid content on the zeta-potential of the liposomes is shown in FIG. 2.

Figure 3:
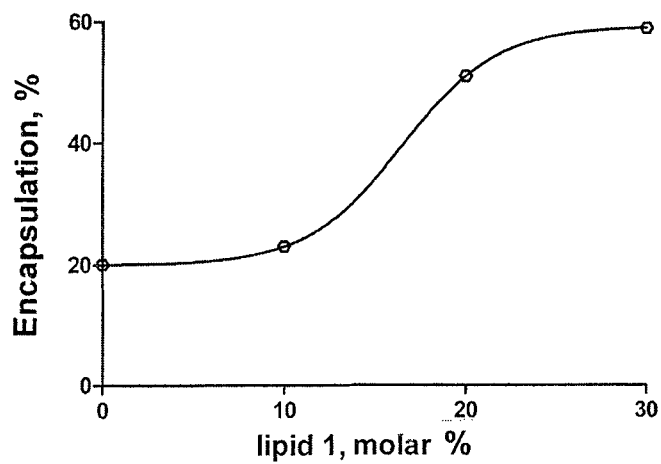
FIG. 3: Dependence of liposomal encapsulation efficiency for Cidofovir on percentage of content (mol. %) of cationic lipid 1 in liposomes.

Due to the strong electrostatic interaction between the positively charged polyamine group of the phospholipids in the liposomal membrane and the negatively charged phosphate or phosphonate group of the drug, the increase of the zeta-potential results in a significantly higher encapsulation efficiency for the anionic analogues of nucleotides. The dependence of the encapsulation efficiency on an increasing content of the cationic lipid is reported in FIG. 3. Whereas in neutral liposomes only passive encapsulation occurs resulting in the encapsulation efficiency about 20%, the value of the encapsulation efficiency of the cationic liposomes is increased three times.

Example 20

Cytotoxicity of Cationic Liposomes

Figure 4A:
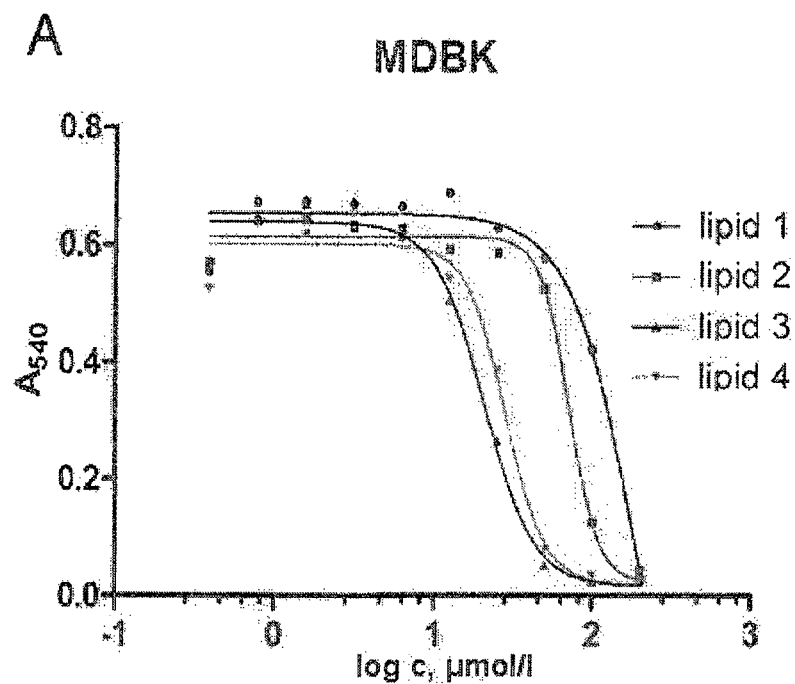
FIG. 4 A,B,C: Toxicity of cationic lipids 1, 2, 3, and 4 to cell lines MDBK-1 (A), B16F10 (B), and MCF-7 (C), respectively.
Figure 4B:
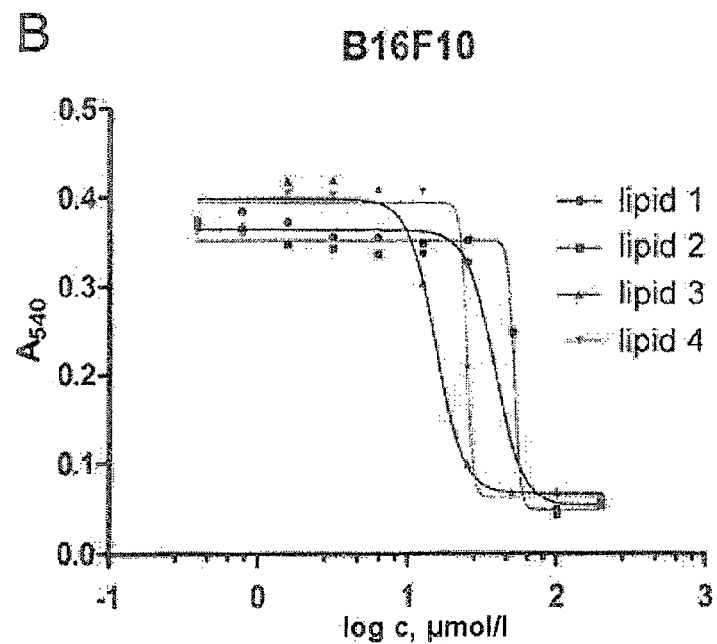
Figure 4C:
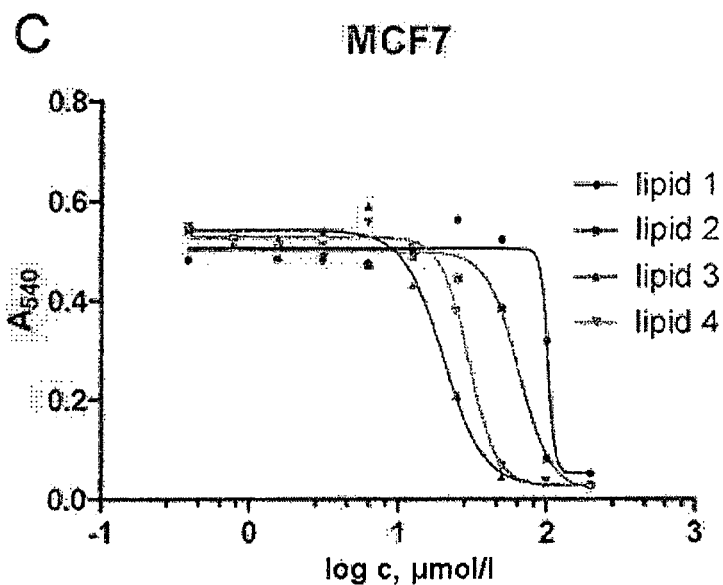
Figure 5:
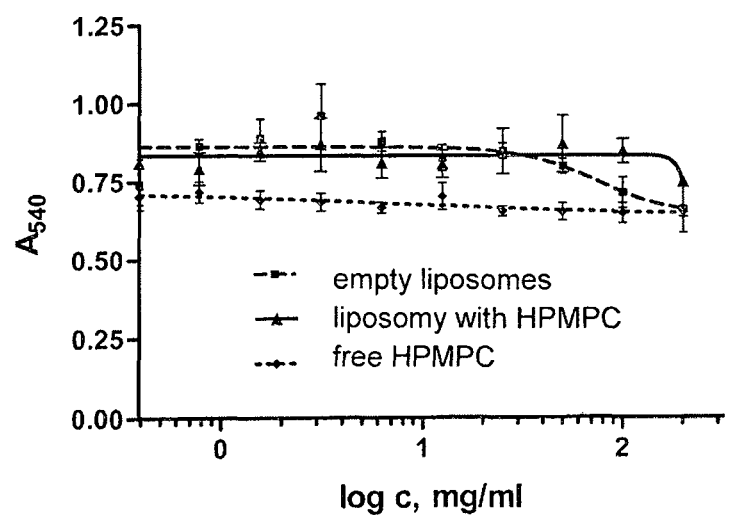
FIG. 5: Cytotoxicity curves for cationic liposomes, cationic liposomes with encapsulated Cidofovir, and for Cidofovir itself, respectively.

Methods:

For the determination of cytotoxicity, the standard MTT cytotoxicity test was used together with microscopic analysis. The cells were incubated with the liposomes for 24 hours. The concentration of total lipid is reported in mg/ml. The tests were carried out with the cell lines MDBK, B16F10, and MCF-7 (FIG. 4).

Results:

The tested cationic lipids in a liposome formulation exert no significant in vitro cytotoxic effect on the cell lines. On the contrary, free cationic lipids in the form of micelles show cytotoxicity in the concentration range of 10-100 μM. A cytotoxic effect of the liposome formulation (the cationic lipid content of 20 mol. %) occurs at the total lipid concentrations above 10 mg/ml. These levels are far exceeding the concentrations used for in vitro applications. In the liposomal formulations, the toxicity of the cationic lipids is significantly decreased, as documented by the curves of in vitro cytotoxicity of the liposomal lipid 1 on the MDBK cell lines (FIG. 4). The cytotoxicity curves of plain liposomes are compared with those of the encapsulated and free Cidofovir. No toxicity was observed up to the lipid concentration of 100 mg/ml. The encapsulation of Cidofovir does not influence the cytotoxicity.

Example 21

In Vitro Antiviral Effect on the BHV-1-Virus Infected MDBK Cells

Methods:

The antiviral effect was tested on in vitro model of MDBK cell line infected by bovine herpes virus 1 (BHV-1). This model provides several advantages for the tests of antiviral effect. The BHV-1 virus can be cultured on the MDBK cell line but cannot be spread to a human. The quantification of viral infection is possible either by the evaluation of cytopathic effect or it is evaluable very precisely by QRT-PCR. The cells were incubated for 6 hours with the tested preparations, then the medium was changed and the cells were infected by the BHV 1 of various titres ($10^{-3}$, $10^{-5}$, $10^{-7}$, $10^{-9}$). The production of the viral DNA was quantified by a standard test of quantitative PCR (polymerase chain reaction) in a real time (QRT-PCR).

Figure 6:
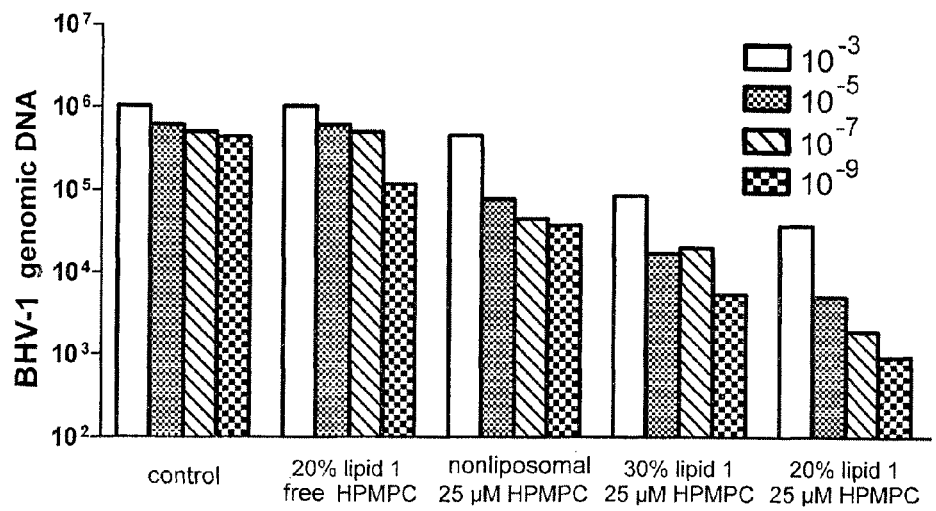
FIG. 6: Antiviral effect of empty cationic liposomes, free Cidofovir, encapsulated Cidofovir in liposomes with 20 and 30 mol. % lipid content (column graphs for the given virus titres ($10^{-3}$, $10^{-5}$, $10^{-7}$, and 109)), respectively.

Results:

The cationic liposomes represent a suitable carrier system for hydrophilic antiviral drugs based on the nucleotide derivatives (e.g. Cidofovir). Compared with free Cidofovir, the liposomal Cidofovir formulation enhances the in vitro antiviral effect against BHV 1 by more than two orders of magnitude (FIG. 6). After the liposomal drug has rapidly penetrated into a cell, it inhibits the synthesis of viral DNA, which results in the production of defected viral particles that are not capable of infecting further cells.

The viral DNA was quantified by QRT-PCR method.

The cationic lipid 1 is denoted by the abbreviation LD1. The content of cationic lipids in the prepared liposomes was 20 mol. % (the example reported here relates to the lipid 1). The MDBK cells were incubated for 6 hours with individual preparations. Afterwards, the medium was changed and the cells were infected by the BHV 1. The production of viral DNA was quantified by QRT-PCR for 24 hours.

Example 22

Enhancement of the Oligonucleotide Internalization Using Cationic Liposomes

Figure 7:
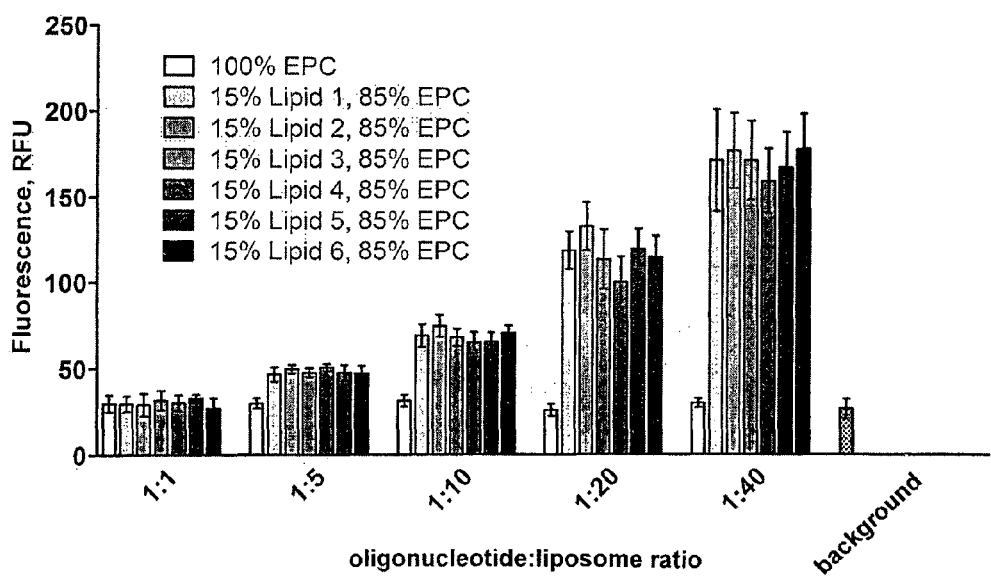
FIG. 7: Non-normalized transfection activity of different types of cationic liposomes. Liposomes prepared from cationic lipids 4 and 2 have shown transfection activity for nucleotides. (The values in the chart represent an average of a triplicate±SD. The amount of oligonucleotide for a well was 500 ng.). EPC=egg phosphatidyl choline
Figure 8:
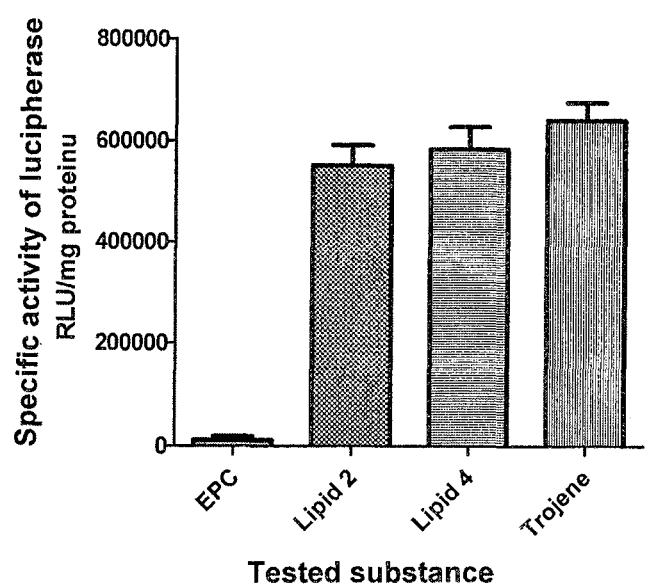
FIG. 8: Transfection efficiency of cationic liposomes to a lucipherase encoding plasmide. EPC=egg phosphatidyl choline, Trojene=liposomal transfection kit.

Methods:

Cationic liposomes were prepared from EPC (85 mol. %) and the cationic lipids 1-6 (15 mol. %). This ratio proved optimal for the transfection of the nucleotides. The transfection efficiency was tested on a standard in vitro model with the cell line of MCF-7. The cells were cultured with serum in 48-well cell culture plates for 24 hours. The concentration range of the liposomes was achieved by stepwise dilution by Opti-MEM Medium (Life Technologies Corporation, Invitrogen™). Afterwards, the oligonucleotides (in Opti-MEM Medium) labelled by FAM (ss 32-mer) were added. The liposomes were mixed with the oligonucleotides and shaken for 20 min, then centrifuged and incubated for 30 minutes. Afterwards, the complex of liposomes and the oligonucleotides was added dropwise to the cells into fresh (i.e. previously changed) Opti-MEM Medium. The cells were incubated for next 24 hours and washed with PBS. CellScrub buffer was added to wash out the liposome/oligonucleotide complexes attached to membranes. This was followed by one more washing step with PBS. Afterwards, the cells were lysed with 1× Cell Culture Lysis Reagent (Promega) under vigorous stirring at the ambient temperature for 30 min. The lysate was subjected to a protein assay by a modified Lowry method. The oligonucleotides were quantified fluorometrically in 96-well cell culture plates. The values of fluorescence were normalized to the total protein concentration (FIG. 7).

Results:

The liposomes prepared from the cationic lipids 1 to 6 show the capability of delivery the oligonucleotides (like the low-molecular nucleotide antiviral drug Cidifovir) into the targeted cells. Neutral liposomes prepared of solely egg phosphatidyl choline do not show such a capability.

Example 23

Transfection of Plasmid

Methods:

Lipopolyamines were applied to the preparation of transfection liposomes composed of cationic lipid and DOPE (DOPE—dioleoyl phosphatidyl ethanolamin) at the ratio of 1:1. The liposomes were prepared by the method of lipid film hydration followed by extrusion through polycarbonate filters. Luciferase-coding plasmid was used for the transfection. The transfection was carried out by the standard test on the MCF 7 cells (150000 bb/j. in 500 μl OptiMEM). The test was carried out in 24-well cell culture plates at cell confluence of 90-95%. After 24-h cultivation, the transfection efficiency was determined by the measurement of luminescence on a microplate luminometer. The complexes of cationic liposomes with DNA were prepared at the ratios of DNA (μg): liposomes (μg) of 1:1, 1:5, 1:10, 1:15, 1:20, 1:30, 1:50, 1:70. The liposomal transfection kit Trojene® (Avanti Polar lipids, USA) was used as the control. The transfection with Trojene® was accomplished according to the manufacturer's instructions.

Results:

The transfection efficiency was demonstrated for the lipids 2 and 4 that possess a bulky hydrophobic cholesteryl moiety. For the transfection of pDNA, these lipids are the most suitable. The liposomes prepared of these cationic lipids demonstrated transfection efficiency comparable with the efficiency of the liposomal transfection kit Trojene®. However, these new lipids exerted lower in vitro cytotoxicity.

The invention claimed is:

1. Lipopolyamines of spermine type of general formula I

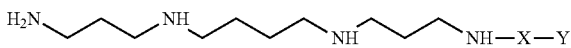

I wherein X is selected from the group containing
C—N bond;
aminopolyethyleneglycol carboxamide linker of general formula II

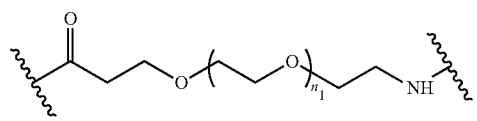

II wherein $n_1$=1-13;
and a hydrophobic domain Y is selected from an acyl having general formula V

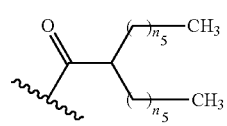

V wherein $n_5$=5-30.

2. Lipopolyamines of spermine type of general formula I according to claim 1, characterized in that X is C—N bond or the linker of general formula II wherein $n_1$=3, and Y is the acyl of general formula V wherein $n_5$=13.

3. A method of preparation of the lipopolyamines of spermine type of general formula I according to claim 1, characterized in that
in a first step, acids selected from the group containing fatty acids of general formula VII

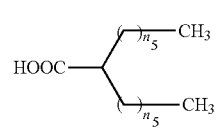

VII wherein $n_1$=5-30;
acids of general formula VIII

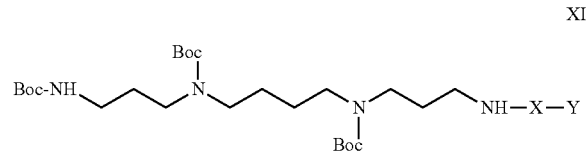

VIII wherein $n_1$=1-13 and $n_5$=5-30;
are converted into their pentafluorophenyl esters by reaction with (pentafluorophenyl)carbonate in the presence of organic base in polar aprotic solvent,
in a second step, the acid pentafluorophenyl esters obtained in the first step are converted by reaction with $N^2N^3N^4$-tri-(tert-butoxycarbonyl)spermine in organic aprotic solvent in the presence of organic base into protected polycationic lipids of general formula XI

XI

Boc-NH~~~~~N(Boc)~~~~N(Boc)~~~~NH—X—Y wherein X and Y are as defined in claim 1,
in a third step, the protected polycationic lipids of general formula XI obtained in the second step are converted by debocylation into lipopolyamines of general formula I as defined in claim 1.

4. The method according to claim 3, wherein the acids of general formula VIII are prepared by basic catalysed reaction of pentafluorophenyl esters of the acids of general formula VII with aminopolyethyleneglycol carboxylic acids of formula $H_2N$—$(CH_2)_2$—O—$[(CH_2)_2$—O$]_n$—$(CH_2)$—COOH, wherein n=1-13, in organic aprotic solvent.

5. A method drug delivery, comprising the steps of:
making a polycationic self-assembling system, further comprising the step of providing a lipopolyamine of spermine type of general formula I, as described in claim 1;
providing a drug;
using the polycationic self-assembling system as a carrier for the drug; and
delivering the drug to a subject in need thereof.

* * * * *